US007323307B2

(12) United States Patent
Lockhart et al.

(10) Patent No.: US 7,323,307 B2
(45) Date of Patent: Jan. 29, 2008

(54) IDENTIFICATION OF MOLECULAR SEQUENCE SIGNATURES AND METHODS INVOLVING THE SAME

(75) Inventors: David J. Lockhart, Del Mar, CA (US); Gordon G. Wong, Brookline, MA (US); Pennina Langer-Safer, Rehovot (IL)

(73) Assignee: Affymetrix, Inc., Santa Clara, CA (US)

( * ) Notice: Subject to any disclaimer, the term of this patent is extended or adjusted under 35 U.S.C. 154(b) by 383 days.

(21) Appl. No.: 10/911,065

(22) Filed: Aug. 4, 2004

(65) Prior Publication Data

US 2005/0069927 A1 Mar. 31, 2005

Related U.S. Application Data

(63) Continuation of application No. 10/099,422, filed on Mar. 14, 2002, now Pat. No. 7,135,285, which is a continuation-in-part of application No. 08/933,219, filed on Sep. 18, 1997, now Pat. No. 6,329,140, which is a continuation of application No. 09/321,481, filed on May 27, 1999, now Pat. No. 6,391,550.

(60) Provisional application No. 60/025,740, filed on Sep. 19, 1996.

(51) Int. Cl.
*C12Q 1/68* (2006.01)
*C07H 21/02* (2006.01)
*C07H 21/04* (2006.01)

(52) U.S. Cl. ........................ 435/6; 536/23.1; 536/24.3

(58) Field of Classification Search .................... 435/6; 536/23.1, 24.3
See application file for complete search history.

(56) References Cited

U.S. PATENT DOCUMENTS

| | | |
|---|---|---|
| 4,656,127 A | 4/1987 | Mundy |
| 4,683,195 A | 7/1987 | Mullis et al. |
| 5,002,867 A | 3/1991 | Macevicz |
| 5,043,272 A | 8/1991 | Hartley |
| 5,057,410 A | 10/1991 | Kawasaki et al. |
| 5,122,599 A | 6/1992 | Barnett et al. .................. 536/27 |
| 5,143,854 A | 9/1992 | Pirrung et al. |
| 5,202,231 A | 4/1993 | Drmanac et al. .............. 435/6 |
| 5,206,137 A | 4/1993 | Ip et al. |
| 5,273,632 A | 12/1993 | Stockham et al. |
| 5,292,639 A | 3/1994 | Beitz et al. |
| 5,436,327 A | 7/1995 | Southern et al. ......... 536/25.34 |
| 5,445,934 A | 8/1995 | Fodor et al. |
| 5,468,610 A | 11/1995 | Polymeropoulos et al. |
| 5,472,842 A | 12/1995 | Stokke et al. |
| 5,474,796 A | 12/1995 | Brennan |
| 5,492,806 A | 2/1996 | Drmanac et al. .............. 435/6 |
| 5,503,976 A | 4/1996 | Mach et al. .................... 435/6 |
| 5,525,464 A | 6/1996 | Drmanac et al. .............. 435/6 |
| 5,525,487 A | 6/1996 | Gallatin et al. ............ 435/69.1 |
| 5,527,681 A | 6/1996 | Holmes |
| 5,547,839 A | 8/1996 | Dower et al. .................. 435/6 |
| 5,567,809 A | 10/1996 | Apple et al. |
| 5,580,970 A | 12/1996 | Hendricks et al. |
| 5,620,848 A | 4/1997 | Levine et al. |
| 5,660,979 A | 8/1997 | Romano et al. |
| 5,667,667 A | 9/1997 | Southern ..................... 205/687 |
| 5,667,972 A | 9/1997 | Drmanac et al. .............. 435/6 |
| 5,670,314 A | 9/1997 | Christman et al. |
| 5,681,942 A | 10/1997 | Buchwald et al. |
| 5,683,872 A | 11/1997 | Rudert |
| 5,690,894 A | 11/1997 | Pinkel et al. |
| 5,695,940 A | 12/1997 | Drmanac et al. .............. 435/6 |
| 5,700,637 A | 12/1997 | Southern ....................... 435/6 |
| 5,744,305 A | 4/1998 | Fodor et al. ................... 435/6 |
| 5,795,716 A | 8/1998 | Chee et al. |
| 5,807,522 A | 9/1998 | Brown et al. ................. 422/50 |
| 5,834,181 A | 11/1998 | Shuber |
| 5,837,832 A | 11/1998 | Chee et al. |
| 5,858,659 A | 1/1999 | Sapolsky et al. |
| 5,861,242 A | 1/1999 | Chee et al. .................... 435/5 |
| 5,902,723 A | 5/1999 | Dower et al. .................. 435/6 |

(Continued)

FOREIGN PATENT DOCUMENTS

EP 0 392 546 10/1990

(Continued)

OTHER PUBLICATIONS

Bugawan et al., "A method for typing polymorphism at the HLA-A locus using PCR amplification and immobilized oligonucleotide probes", *Tissue Antigens*, vol. 44, 1994, pp. 137-147.
Bentley et al., "The Development and Application of Automated Gridding for Efficient Screening of Yeast and Bacterial Ordered Libraries", *Genomics 12*, 1992, pp. 534-541.
Cronin et al., "Amer. Jrnl. Human Genetics", vol. 55, No. 33, 1994, pp. A217 (supplement).
Cardillo et al., *Jrnl. Of Pathology*, citation only, pp. 134A.
Lipshutz et al., "Using Oligonucleotide Probe Arrays to Access Genetic Diversity", *BioTechniques*, vol. 19, No. 3, 1995, pp. 442-447.
Maskos et al., "A novel method for the parallel analysis of multiple sequence variants by hybridisation to oligonucleotides", *Nucleic Acids Research*, vol. 21, No. 9, 1993, pp. 2267-2268.

(Continued)

*Primary Examiner*—Ethan Whisenant
(74) *Attorney, Agent, or Firm*—Philip L. McGarrigle

(57) ABSTRACT

Novel means and methods for analyzing hybridization data derived from hybridization assays between a target nucleic acid and differently sequenced polynucleotide probes involve selecting probe sets that define reference sequences for sequence signatures and deriving useful data about the nature of the target nucleic acid molecule based on its hybridization to the probes. The methods are useful for determining whether the target contains a nucleic acid or polypeptide sequence signature, whether the target encodes a member of a gene family, or whether the target is derived from one of any number of genes.

9 Claims, 6 Drawing Sheets

U.S. PATENT DOCUMENTS

| | | | |
|---|---|---|---|
| 5,962,221 | A | 10/1999 | Caetano-Anolles ............ 435/6 |
| 5,972,619 | A | 10/1999 | Drmanac et al. ............... 435/6 |
| 6,018,041 | A | 1/2000 | Drmanac et al. .......... 536/24.3 |
| 6,025,136 | A | 2/2000 | Drmanac ........................ 435/6 |
| 6,027,880 | A | 2/2000 | Cronin et al. |
| 6,040,138 | A | 3/2000 | Lockhart et al. ............... 435/6 |
| 6,045,996 | A | 4/2000 | Cronin et al. |
| 6,054,270 | A | 4/2000 | Southern ........................ 435/6 |
| 6,090,566 | A | 7/2000 | Vogelstein et al. |
| 6,171,793 | B1 | 1/2001 | Phillips et al. |
| 6,210,878 | B1 | 4/2001 | Pinkel et al. |
| 6,268,128 | B1 | 7/2001 | Collins et al. |
| 6,309,822 | B1 | 10/2001 | Fodor et al. .................... 435/6 |
| 6,309,823 | B1 | 10/2001 | Cronin et al. |
| 6,329,140 | B1 | 12/2001 | Lockhart et al. |
| 6,391,550 | B1 | 5/2002 | Lockhart et al. |
| 6,468,744 | B1 | 10/2002 | Cronin et al. |
| 6,582,908 | B2 | 7/2003 | Fodor et al. |
| 6,632,605 | B1 | 10/2003 | Cronin et al. |
| 6,881,571 | B1 | 4/2005 | Schweigerhoffer et al. |
| 7,115,364 | B1 | 10/2006 | Chee et al. |
| 7,135,285 | B2 | 11/2006 | Lockhart et al. |
| 2002/0048749 | A1 | 4/2002 | Lipshutz et al. |
| 2003/0054393 | A1 | 3/2003 | Lipshutz et al. |
| 2003/0129604 | A1 | 7/2003 | Lockhart et al. |
| 2003/0165823 | A1 | 9/2003 | Cronin et al. |
| 2003/0165830 | A1 | 9/2003 | Cronin et al. |
| 2005/0064436 | A1 | 3/2005 | Barrett et al. |
| 2006/0229824 | A1 | 10/2006 | Cronin et al. |
| 2006/0263807 | A1 | 11/2006 | Lipshutz et al. |
| 2007/0054286 | A1 | 3/2007 | Cronin et al. |

FOREIGN PATENT DOCUMENTS

| | | |
|---|---|---|
| EP | 0463395 | 1/1992 |
| EP | 0512342 | 11/1992 |
| EP | 0 373 303 | 8/1994 |
| EP | 07171113 | 6/1996 |
| EP | 0785280 | 7/1997 |
| EP | 0950720 | 10/1999 |
| GB | 8810400.5 | 6/1989 |
| WO | WO 89/10977 | 11/1989 |
| WO | WO 89/11548 | 11/1989 |
| WO | WO 90/00626 | 1/1990 |
| WO | WO 90/03382 | 4/1990 |
| WO | WO 91/09226 | 6/1991 |
| WO | WO 91/10745 | 7/1991 |
| WO | WO 92/10092 | 6/1992 |
| WO | WO 92/10588 | 6/1992 |
| WO | WO 93/17126 | 9/1993 |
| WO | WO 94/03638 | 2/1994 |
| WO | WO 95/00530 | 1/1995 |
| WO | WO 95/12607 | 5/1995 |
| WO | WO 9511995 | 5/1995 |
| WO | WO 95/25538 | 9/1995 |
| WO | WO 95/26973 | 10/1995 |
| WO | WO 97/29212 | 8/1997 |
| WO | WO 98/20165 | 5/1998 |
| WO | WO 02/033415 | 4/2002 |
| WO | WO 02/039120 | 5/2002 |
| WO | WO 02/056030 | 7/2002 |
| WO | WO 02/084249 | 10/2002 |

OTHER PUBLICATIONS

Miyada et al., "Detection of cystic fibrosis mutations in a GeneChip™ assay format", *Published Abstracts: Moledular Genetics of Disease*, No. 2125, 1994, pp. A362.

Santamaria et al., "HLA Class I Sequence-Based Typing", *Human Immunology 37*, 1993, pp. 39-50.

Schena et al. "Quantitative Monitorig of Gene Expression Patterns with a Complementary DNA Microarray", Science 270 : 467-470, Oct. 1995.

Yershov et al., "DNA analysis and diagnostics on oligonucleotide microchips", *Proc. Natl. Acad. Sci. USA*, vol. 93, May 1996, pp. 4913-4918.

Beltz G.A. et al; "Isolation of Multigene Families and Determination of Homologies by Filter Hybridization Methods" Methods in Enzymology, Academic Press Inc, San Diego, CA, US, vol. 100, No. Part B., Dec. 1983, pp. 266-285.

Southern E. M. et al: "Analyzing and Comparing Nucleic Acid Sequences by Hybridization to Arrays of Oligonucleotides: Evaluation Using Experimental Models" Genomics, Academic Press, San Diego, US, vol. 13, 1992. pp. 1008-1017.

Hanks S. K. et al; "Use of Degenerate Oligonucleotide Probes to Identify Clones that Encode Protein Kinases" Methods in Enzymology. Academic Press Inc, San Diego. CA, US, vol. 200, 1991, pp. 525-532.

Chee et al., "A New Method for Rapid Sequence Analysis: Detection of HIV Reverse Transcriptase Mutations", HIV Drug Resistance Third International Workshop, Aug. 2-5, 1994, Abstract.

Chee et al., "Accessing Genetic Information with High-Density DNA Arrays", Science, 274:610-614 (1996).

Chee et al., "Genetic Analysis by Hybridization to Sequence-Specific DNA Arrays", American Society of Human Genetics, 43rd Annual Meeting, Oct. 5-9, 1993, Abstract.

Chee et al., "Sequence Analysis by Hybridization: the Human Mitochondrial Genome on a Chip," poster and slide presentation, Genome Sequencing and Analysis Conference V, Sep. 17-21, 1994, Hilton Head, SC (Abstract).

Chee et al., "Sequencing Mitochondrial DNA Polymorphisms by Hybridization", American Society of Human Genetics, 44th Annual Meeting, Oct. 18-22, 1994, Abstract.

Chee et al., "Towards Sequencing Mitochondrial DNA Polymorphisms by Hybridization to a Custom Oligonucleotide Probe Array", American Society of Human Genetics, 43rd Annual Meeting, Oct. 5-9, 1993 abstract.

Chee, "Resequencing DNA by Hybridization to Olignucleotide Arrays", Western Biotech Conference, Oct. 18-21, 1995, Abstract.

Cocco et al., "Lack of Evidence for a Role of the Myelin Basic Protein Gene in Multiple Sclerosis Susceptibility in Sardinian Patients", J. Neurology, 24(11):1552-1555 (2002).

Collins et al., "Variations on a Theme: Cataloging Human DNA Sequence Variation", Science 278: 1580-1581 (1997).

Cronin et al., "GeneChip™ Screening Assay for Cystic Fibrosis Mutations", American Society of Human Genetics Meeting, Oct. 1994, Abstract.

Cronin et al., "Cystic Fibrosis Mutation Detection by Hybridization to Light-Generated DNA Probe Array", Human Mutation, 7(3):244-255 (1996).

Cronin et al., "Hybridization to Arrays of Olignucleotides," poster, Nucleic Acids in Medical Applications Conference sponsored by ACC, Jan. 1993, Abstract.

Cronin et al., "Detecting Cystic Fibrosis Mutations by Hybridization to DNA Probe Arrays," slide presentation, UCSF School of Medicine Symposium: Molecular Approaches to Laboratory I Diagnosis. Feb. 1995, Abstract.

Cronin et al., "Detection of Cystic Fibrosis Gene Mutations by Hybridization to GeneChip Probe Arrays," poster, Nucleic Acids in Medical Applications Conference sponsored by ACC, Nov. 1993.

Elder, "Analysis of DNA Oligonucleotide Hybridization Data by Maximum Entropy," Maximum Entropy and Bayesian Methods, pp. 363-371 (1993).

Fan et al., "Genetic Mapping: Finding and Analyzing Single-Nucleotide Polymorphism with High-Density DNA Arrays", Amer. J. Human Genet. 61 (4):1601 (1997).

Fan, J-B, et al., Screening the Human Genome for Single-Nucleotide Polymorphisms by Hybridization to High-Density Oligonucleotide Arraysn, Mutation Detection 1997, 4th International Workshop, May 29-Jun. 2, 1997, Brno, Czech Republic, one page.

Finch et al., "PCR/RFLP Assay for Copy Number of Mutant and Wild-Type Alleles", BioTechiques, 21:1055-1060 (1996).

Gonzales et al., "Pharmacogenetic Phenotyping and Genotyping, Present Status and Future Potential". Clin. Pharmacokinet, 26(1):59-70 (1994).

Hacia et al., "Detection of Heterozygous Mutations in BRCA1 Using High Density Oligonucleotide Arrays and Two-Colour Fluorescence Analysis", Nature Genetics, 14:441-447 (1996).

Hagstrom et al., "Maximum Likelihood Genetic Sequence Reconstruction form Oligo Content", Networks 24:297-302, (1994).

Kwok, P-Y, et al., "Increasing the Information Content of STS-Based Genome Maps: Identifying Polymorphisms in Maped STS's", Genomics, 31:123-126, Article No. 0019 (1996).

Laan et al., "Solid-Phase Minisequencing Confirmed by FISH Analysis in Determination of Gene Copy Number", Human Genetics, 96:275-280 (1995).

Lipshutz, "Likelihood DNA Sequencing by Hybridization," J. Biomol. Struct. Dyn., 11:637-653 (1993).

Lipshutz, "Olignucleotide Arrays for Hybridization Analysis," poster, Genome Sequencing and Analysis Conference V, Oct. 23-27, 1993, Abstract.

Lobban et al., "DNA Chips for Genetic Analysis", Genome Sequencing and Analysis Conference V, Oct. 23-27, 1993, Abstract.

Lockhart et al., "DNA Sequencing by Hybridization on High Density Probe Arrays: Enzymatic Enhancement and Sequence Reconstruction", American Society of Human Genetics 44th Annual Meeting, Oct. 18-22, 1994.

Luo et al., "Cellular Protein Modulates Effects of Human Immunodeficiency Virus Type 1 Rev," J. Virol. 69:3850-3856 (1994).

Maxam et al., "A New Method for Sequencing DNA," Proc. Natl. Acad. Sci. USA, 74:560-564 (1977).

Maxam et al., "Sequencing End-Labeled DNA with Base-Specific Chemical Cleavages," Methods in Enzymology, 65:499-560 (1980).

Querat et al., "Nucleotide Sequence Analysis of SA-OMVV, a Visna-Related Ovine Lentivirus: Phylogenetic History of Lentiviruses," Virology, 175:434-447 (1990).

Ratner et al., "Complete Nucleotide Sequence of the AIDS Virus, HLTV-III," Nature, 313:277-284 (1985).

Risch et al., "The Future of Genetic Studies of Complex Human Diseases", Science 273:1516-1517 (1996).

Rudert et al., "Rapid Detection of Sequence Variations Using Polymers for Specific Oligonucleoties", Nucl. Acids Res., 20(5): 1146 (1992).

Sambrook et al., "Molecular Cloning," Cold Spring Harbor Press, pp. 11.45-11.47 (1989).

Sanger et al., "DNA Sequencing with Chain-Terminating Inhibitors," Proc. Natl. Acad. Sci. USA, 74:5463-5467 (1977).

Sapolsky et al., "High-Throughput Polymorphism Screening and Genotyping with High-Density Oligonucleotide Arrays", Genetic Analysis: Biomolecular Engineering 14(5-6): 187-192 (1992).

Schena et al., "Quantitative Monitoring of Gene Expression Patterns with a Complementary DNA Microarray," Science 270:467-470 (1995).

Stickland et al., "Quantification of Oncogene Dosage in Tumors by Simultaneous Dual Label Hydridization", Oncogene, 8:223-227 (1993).

Strachan et al., Human Molecular Genetics, pp. 466-471, Bios Scientific Publishers Limited, Oxford OX4 1RE, UK (1996).

Stratagene 1988 Catalog, "Gene Characterization Kits," p. 39.

Takeda et al., An Increased NM23H1 Copy Number May be a Poor Prognostic Factor Independent of LOH on 1p in Neuroblastomasn, Br. J. Cancer, 74:1620-1626 (1996).

Tully et al., "Analysis of 6 VNTR Loci by Multiplex PCR and Automated Fluorescent Detection", Human Genetics, 92:554-562 (1993).

Wain-Hobson et al., "Nucleotide Sequence of the AIDS Virus, LAV," Cell, 40:9-17 (1985).

Wang et al., "Large-Scale Identification, Mapping and Genotyping of Single-Nucleotide Polymorphisms in the Human Genome", Science 280: 1077-1082 (1998).

FIG. 6

```
                              SEQUENCE LISTING

<160> NUMBER OF SEQ ID NOS: 43

<210> SEQ ID NO 1
<211> LENGTH: 15
<212> TYPE: DNA
<213> ORGANISM: Artificial Sequence
<220> FEATURE:
<223> OTHER INFORMATION: Synthetic sequence.

<400> SEQUENCE: 1
attggcaaag ctatg                                                        15

<210> SEQ ID NO 2
<211> LENGTH: 5
<212> TYPE: PRT
<213> ORGANISM: Artificial Sequence
<220> FEATURE:
<223> OTHER INFORMATION: Synthetic sequence.

<400> SEQUENCE: 2

Asn Gly Lys Ala Met
1               5

<210> SEQ ID NO 3
<211> LENGTH: 15
<212> TYPE: DNA
<213> ORGANISM: Artificial Sequence
<220> FEATURE:
<223> OTHER INFORMATION: Synthetic sequence.

<400> SEQUENCE: 3
aacggaaagg caatg                                                        15

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence.

<400> SEQUENCE: 4

Arg Arg Gly Ser Phe
1               5

<210> SEQ ID NO 5
<211> LENGTH: 15
<212> TYPE: DNA
<213> ORGANISM: Artificial Sequence
<220> FEATURE:
<223> OTHER INFORMATION: Synthetic sequence.

<400> SEQUENCE: 5
```
cgccgcggaa gtttt                                                    15

<210> SEQ ID NO 6
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g
<220> FEATURE:
<221> NAME/KEY: misc_feature
<222> LOCATION: (84)..(84)
<223> OTHER INFORMATION: n = A,T,C or G

<400> SEQUENCE: 6
gcggtcgtca aggcgcagga cagccaccgc ngccgcggag gccaactgcc gggacnaact    60
actgcgatgg ggagtgcccc ttcngaggcc tgtggctgca gc                       102

<210> SEQ ID NO 7
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 7
catgatggaa aagggcatcc tctccacaaa ncaagccaaa cacaaacagc ggaaantttt    60
actgccacgg agaatgccct tttngagggt tgtgggtgtc gc                       102

<210> SEQ ID NO 8
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 8
cacatcagag ctgccctttc cattgagcgg ntctactggg gtcttgctgc ctctgntatt    60
attgctctgg agcatgccag ttcngagtct tgcgcttgca ga                       102

<210> SEQ ID NO 9
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 9
ggccggggcc atgccttgac ccgacgccgg nagccctaag catcactcac agcggnttct      60
actgccatgg ggactgcccc tttngaggga tgtgggtgcc gc                        102

<210> SEQ ID NO 10
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c, or g
<220> FEATURE:
<221> NAME/KEY: misc_feature
<222> LOCATION: (56)..(56)
<223> OTHER INFORMATION: n=a,t,c, or g
<220> FEATURE:
<221> NAME/KEY: misc_feature
<222> LOCATION: (84)..(84)
<223> OTHER INFORMATION: n=a,t,c, or g

<400> SEQUENCE: 10
gccttcttca aggcgagtga ggtacttctt ngcagccaac aaacgaaaaa atcaantttt      60
attgtgatgg agaatgttct tttncgctca tgtggctgcc ac                        102

<210> SEQ ID NO 11
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 11
gctttcttca aagtgagtga ggtccacgtg ntcagcctcc agccggcgcc gacaanaatt      60
actgtgatgg agaatgctcc ttcnagagct tgtggatgcc ac                        102

<210> SEQ ID NO 12
<211> LENGTH: 102
<212> TYPE: DNA
<213> ORGANISM: Homo sapiens
<220> FEATURE:
<221> NAME/KEY: misc_feature
<222> LOCATION: (31)..(31)

<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 12
gctttcttca aggccacgga ggtccacttc ntccacgggg agcaaacagc gcagcntact    60
actgtgaggg ggagtgtgcc ttcncgggcc tgtggctgcc ac                     102

<210> SEQ ID NO 13
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 13
actttcttca gggccagtcc gagtcccatc ngcagtgagg ccactgagga ggaggntatt    60
actgtgaggg ggagtgctcc ttcnaaggcc tgcggctgcc ac                     102

<210> SEQ ID NO 14
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 14
ggatacacag ctgtgggacc acttttagcc nagcgccggg gctggcagcc actgtntacg    60
agtgtaaggg cggctgcttc ttcngcagag tgtgggtgca gg                     102

<210> SEQ ID NO 15
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 15
agatcaaaca tcatctatga ctccactgcc naacgccaaa ggaaactact gtaagntatg    60
aatgccgtgg tgtttgtaac tacntccgaa tgtggctgta ga                     102

<210> SEQ ID NO 16
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 16
atggagcttc gagtcctaga gaacacaaaa naacctgggt ctggactgcg acgagnaact    60
actgctccgg ccagtgcgag tacngatcgc tgtggctgct ct                     102

<210> SEQ ID NO 17
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 17
gcgtcgccaa gggcagtcat tggcggccgc nacggcgttg gccgggacgc ggacantacc    60
actgcgaggg cctttgcgac ttcngaggcc tgcggctgca gg                     102

<210> SEQ ID NO 18
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 18
gccaggcctt ggctgccctc gcccggccgc nacggccttc gccagtcgcc atggcntatc    60

```
actgcgaggg tgtatgcgac ttcngagtcg tgcggctgca gg                      102
```

<210> SEQ ID NO 19
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 19

```
cggatccgag ccaatgagcc tggagcaggc naggacccccc acctgtgagc ctgcgnaatt    60
actgcagtgg gcagtgccct cccngaggcc tgtggctgca gc                      102
```

<210> SEQ ID NO 20
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 20

```
gaggagttca tggaaaggga atctcttctc ncaagcagat ggtatctcag ctgagnaact    60
actgtaaagg aacttgtctc cgangagtct tgtacatgca ga                      102
```

<210> SEQ ID NO 21
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 21

```
ctcgacccgc gcctgtgcca cccctggcc ngacgccgaa cccgtgttgg gcggcnaact     60
actgccaggg tcagtgcgcg ctgngacgag tgcggctgcc gc                      102
```

<210> SEQ ID NO 22
<211> LENGTH: 102
<212> TYPE: DNA
<213> ORGANISM: Homo sapiens

```
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 22
accgtgtatg agtacctgtt cagccagcgg ngccccactg gccactcgcc agggcnttcc      60
actgcgaggg gctgtgcgag ttcngagtcg tgtggctgca gg                        102

<210> SEQ ID NO 23
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 23
ttagaggtca aggtaacaga cacaccaaaa ngattttggt cttgactgtg atgagnaatt      60
catgctctgg agagtgtgaa tttngaccgc tgtgggtgct ca                        102

<210> SEQ ID NO 24
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 24
gaggaagcta ctgaggtgga aagatctccc ngggcagaaa gccatccgct ccgaanaggt      60
actgtaaagg ggactgtcct aggnacgagg tgcacctgtc gt                        102

<210> SEQ ID NO 25
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
```

```
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 25
ctggactttg acgagaagac gatgcagaaa ncagtgggat gagccccggg tctgcntact      60
actgtgctgg ggcctgcgag ttcngagacc tgtgcctgtc gg                        102

<210> SEQ ID NO 26
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t, c or g
<220> FEATURE:
<221> NAME/KEY: misc_feature
<222> LOCATION: (56)..(56)
<223> OTHER INFORMATION: n=a,t, c or g
<220> FEATURE:
<221> NAME/KEY: misc_feature
<222> LOCATION: (84)..(84)
<223> OTHER INFORMATION: n=a,t, c or g

<400> SEQUENCE: 26
gtcatggatt ttattcaagc caccattaaa ntcaccagat aaacaaatgg cagtgnaggt      60
actgcagcgg ctcttgcgat gcanaaaagg tgtggatgta tc                        102

<210> SEQ ID NO 27
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 27
actctcaacc ctgatcagtg ccaccttct ngcagccatc cctgccccca agcttnaatt       60
actgccatgg agagtgtccc ttcngatgaa tgtgggtgtg gg                        102

<210> SEQ ID NO 28
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 28
```

```
actcggacca gaccacccag tggaggggag ntcaactccc ctgatgtcct ggcctncact      60
actgtcatgg tggttgtggg ctgncagcac tgtgcttgta tc                       102
```

<210> SEQ ID NO 29
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 29

```
gcccggcagt ctgaagacca ccctcatcgc nggcttggag tgtgatggca aggtcnaact      60
actgcgaggg tgagtgcccg agcngaggag tgtgggtgct ca                       102
```

<210> SEQ ID NO 30
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 30

```
caggctcggc tgggcgacag caggcaccgc nggcctggag tgcgatggcc ggaccnaact      60
actgtgaggg cagctgccca gccngaggag tgcggctgcg cc                       102
```

<210> SEQ ID NO 31
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 31

```
gcccgggtga gagttgggggg caaacaccag nggcatcgac tgccaaggag ggtccnaact     60
tctgcatagg gcagtgccca ctangaggcc tgtgggtgca gt                       102
```

<210> SEQ ID NO 32

<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 32
tggcgcgggc gggatccgcg cgggccgggt nagcgcgggg gccaccgccg ccgacnaaca     60
attgccaggg cgtgtgcggc tggnaccgag tgtggctgcc gg                       102

<210> SEQ ID NO 33
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 33
ctgtctgtag agaggggcgg atggggcaga ncatcatttg ccagacagaa gccaantatc     60
gctgtgaggg cgagtgtcct aacngaggag tgtgggtgcc tc                       102

<210> SEQ ID NO 34
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 34
ttaactgata gggaatcttc ttttctcatg ncaagcatgc agcattgaat ctgatnaatt     60
actgtaaagg aatctgtact cggncagtcc tgtacatgta ga                       102

<210> SEQ ID NO 35
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g

```
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 35
ggtttcttca gggccaacca gagtcctgtg nacagcaaga ccactgaaga agaagntatt      60
actgtgctgg ggagtgcatc tacncaggcc tgtggctgcc ac                       102

<210> SEQ ID NO 36
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 36
ctggagaggg cccagcatct gcaaagctcc ngccctggac accaactatt gcttcnaact      60
tctgcctcgg gccctgcccc tacncgctcc tgcaagtgca gc                       102

<210> SEQ ID NO 37
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
<223> OTHER INFORMATION: n=a,t,c or g

<400> SEQUENCE: 37
tacagacttg agtcacaaca gaccaaccgg ngctttggat gcggcctatt gctttnaact      60
tctgtgctgg agcatgcccg tatnaagtct tgcaaatgca gc                       102

<210> SEQ ID NO 38
<211> LENGTH: 102
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n=a,t,c or g
<220> FEATURE:
<221> NAME/KEY: misc_feature
<222> LOCATION: (56)..(56)
<223> OTHER INFORMATION: n=a,t,c or g
<220> FEATURE:
<221> NAME/KEY: misc_feature
<222> LOCATION: (84)..(84)
```

-continued

```
<223> OTHER INFORMATION: n=a,t,c or g

<400> SEQUENCE: 38
cggctcgaca acccgggcca gggggtcag ngctttggac accaattact gcttcnaact      60
tctgctcagg cccttgccca tacnaagtct tgtaaatgta gc                       102

<210> SEQ ID NO 39
<211> LENGTH: 5
<212> TYPE: PRT
<213> ORGANISM: Artificial Sequence
<220> FEATURE:
<223> OTHER INFORMATION: Synthetic sequence.

<400> SEQUENCE: 39

Arg Arg Gly Ser Val
1               5

<210> SEQ ID NO 40
<211> LENGTH: 15
<212> TYPE: DNA
<213> ORGANISM: Artificial Sequence
<220> FEATURE:
<223> OTHER INFORMATION: Synthetic sequence.

<400> SEQUENCE: 40
cgacgagggt ctgtc                                                      15

<210> SEQ ID NO 41
<211> LENGTH: 15
<212> TYPE: DNA
<213> ORGANISM: Artificial Sequence
<220> FEATURE:
<223> OTHER INFORMATION: Synthetic sequence.

<400> SEQUENCE: 41
cgccgagggt ccggg                                                      15

<210> SEQ ID NO 42
<211> LENGTH: 15
<212> TYPE: DNA
<213> ORGANISM: Artificial Sequence
<220> FEATURE:
<223> OTHER INFORMATION: Synthetic sequence.

<400> SEQUENCE: 42
cgacgatggt ctgtc                                                      15

<210> SEQ ID NO 43
<211> LENGTH: 5
<212> TYPE: PRT
<213> ORGANISM: Artificial Sequence
<220> FEATURE:
<223> OTHER INFORMATION: Synthetic sequence.

<400> SEQUENCE: 43

Arg Arg Trp Ser Val
1               5
```

IDENTIFICATION OF MOLECULAR SEQUENCE SIGNATURES AND METHODS INVOLVING THE SAME

CROSS REFERENCE TO RELATED APPLICATIONS

This application is a continuation of U.S. patent application Ser. No. 10/099,442, filed Mar. 14, 2002, now U.S. Pat. No. 7,135,285, which is a continuation-in-part of and claims the benefit of the filing date of U.S. patent application Ser. No. 08/933,219, filed Sep. 18, 1997, now U.S. Pat. No. 6,329,140, which claims the benefit of the filing date of U.S. provisional patent application No. 60/025,740, filed Sep. 19, 1996, which is incorporated herein in its entirety.

BACKGROUND OF THE INVENTION

This invention relates to methods and means for rapid screening of target nucleic acid molecules for the presence of sequence signatures. In preferred embodiments, hybridization data is processed by a programmable digital computer.

Polynucleotide arrays, such as the GeneChip® array (Affymetrix, Inc., Santa Clara, Calif., USA), can contain many thousands of differently sequenced polynucleotide probes at feature densities greater than five hundred thousand per 1 cm$^2$. Such arrays enable one to obtain nucleotide sequence information from target nucleic acid molecules. The information is obtained by performing a hybridization reaction between the target nucleic acid molecule and the polynucleotide probes on the polynucleotide array. The location and identity of the probes to which the target has hybridized, and the extent of hybridization, is determined. Because hybridization between nucleic acids is a function of their sequences, analysis of the sequence of the probes to which the target has hybridized, as well as the extent of hybridization, provides information about the sequence of the target molecule.

Because polynucleotide arrays can have many thousands of probes, hybridization reactions create large amounts of raw data for analysis. Already, several ways of processing such data have been developed. In one application, one examines hybridization between a target molecule and a set of probes that are based upon a reference nucleotide sequence. Probes in the set to which the target does not hybridize or hybridizes weakly indicate sequences in which the target differs from the reference sequence. Nucleic acid arrays have been used to interrogate single nucleotide differences between reference and target nucleic acid sequences: Examples include the identification of genetic variants of infectious agents, such as HIV, or genes associated with human genetic diseases, such as cystic fibrosis.

Other ways of obtaining useful information from hybridization data would be of benefit to the scientific and medical communities.

SUMMARY OF THE INVENTION

The present invention involves a hierarchical method of array-based analysis in which single nucleotide base determination may or may not be one step. The present invention has several embodiments, many of which involve the determination of a sequence signature. Useful sequence signatures include polynucleotide or polypeptide sequence signatures, such as those defining protein domains, gene families, different genes in a genome, repeat sequences, or polymorphic forms of a gene. The methods involve performing hybridization assays between the target nucleic acid molecules to be screened and polynucleotide arrays designed to identify targets that contain the sequence signatures. The arrays contain probe sets. The probes in a set, taken together, represent the sequence of the sequence signature, or variations upon that sequence. Thereby, the probes define the reference sequence signature and sequences related to the sequence signature. A hybridization assay between the target molecule and the probes in the array generates data about which probes the target has hybridized to. The extent of hybridization may likewise be determined. Computer programs are then used to process the data. By determining whether the target has hybridized to probes defining one or more reference sequences, or to probes defining sequences that deviate from the reference sequences, one can determine whether the target has the same sequence or a sequence similar to one or more of the reference sequences. By selecting appropriate reference sequences to put on the array as probes, one can determine whether a target encodes a particular closely related polypeptide sequence signature, is a member of a gene family, or has the sequence of a particular or closely related gene in the genome. One can also look at patterns of differences between target and reference sequences to identify novel gene families, new members of gene families, and the like. By identifying the similarities and/or differences between the reference and target sequences, one can also determine the position on the chromosome of a target nucleic acid molecule.

To determine whether a target nucleic acid molecule contains a sequence signature, the following steps can be employed: providing a polynucleotide array comprising a set of polynucleotide probes that define the sequence signature; generating hybridization data by performing a hybridization reaction between the target nucleic acid molecule and the probes in the set and detecting hybridization between the target nucleic acid molecule and each of the probes in the set; and processing the hybridization data to determine whether the target nucleic acid molecule has the sequence signature. In certain embodiments, the sequence signature is a polypeptide sequence signature; the sequence signature contains variable positions; and the step of processing is performed by a programmable digital computer. In another embodiment, if the sequence signature is an amino acid sequence signature, the array comprises sets of probes that define the degenerate set of nucleotide sequence signatures encoding the polypeptide sequence signature. In addition, or as an alternative to degenerate probe sets, useful probe sets can contain inosine, other generic bases, or mixtures of A, C, T, G at the 3d position of a codon site. Probe sets can also contain sequences that query the presence of polymorphic variants of a sequence signature.

One aspect of the invention provides a method of analyzing a nucleic acid sample, comprising selecting a hierarchy of assay techniques comprising at least a first and second assay. The first assay is selected to provide a determination of the presence or absence or variant of a first sequence signature and the second assay is selected to provide a determination of the presence or absence or variant of a second sequence signature. At least one of the assays employs a high-density nucleic acid array. One analyzes the nucleic acid sample using the first assay. One may then opt to analyze the nucleic acid sample in a second assay depending upon the results of the first assay.

In a further embodiment, the first or second sequence signature is a conserved region of a gene family. In certain embodiments, the first or second sequence signature is a non-conserved region of a gene family. The method can additionally comprise determining the full length sequence of said nucleic acid target.

The present invention also provides a method of selecting clones for analysis. This aspect of the invention provides a support having a variety of clones associated with it. The support is exposed to one or more polynucleotides under low, medium, or high stringency conditions to permit at least some hybridization between the clones and the polynucleotides. One identifies the clones that hybridize with the polynucleotides. Clones selected for analysis are those not identified as hybridizing to the polynucleotides. In one embodiment of this method, the support is a high-density nucleic acid array.

Also provided is a method of screening a nucleic acid sample for analysis. The steps are: providing a sample containing nucleic acids; analyzing whether the sample contains a sequence signature using a high-density nucleic acid array; and further analyzing the nucleic acid sample only if that sequence signature is not present.

This invention also provides a method for determining whether a target molecule has a sequence from a gene family member. The method involves providing a polynucleotide array comprising, for each of at least two different gene family members, a set of polynucleotide probes that define a reference nucleotide sequence from the region of the gene family member; generating hybridization data by performing a hybridization reaction between the target nucleic acid molecule and the probes in the sets and detecting hybridization between the target nucleic acid molecule and each of the probes in the sets; and processing the hybridization data to determine whether the target nucleic acid has the reference sequence from one of the gene family members.

In one embodiment, the step of selecting the target nucleic acid molecule is performed by determining whether the target hybridizes to a nucleic acid probe that hybridizes to a gene encoding the gene family members. In another embodiment, the step of processing is performed by a programmable digital computer. In another embodiment, the polynucleotide array further comprises, for each of the gene family members, a probe set defining a highly conserved region of the gene and a probe set defining a highly variable region of the gene. In a further embodiment, the polynucleotide array further comprises, for each of the gene family members, probe sets defining at least two highly conserved regions of the gene and probe sets defining at least two highly variable regions of the gene. In another embodiment, the reference nucleotide sequence codes for an amino acid sequence and the array further comprises probe sets capable of defining the different nucleotide sequences encoding the amino acid sequence. In one embodiment, the method further comprises the step of determining the nucleotide sequence of the target nucleic acid molecule if the target does not have the chosen signature sequence of the gene family member.

In another aspect, the invention provides a computer program product for analyzing hybridization data comprising: code that receives as input the sequence of a polynucleotide probe in each feature of a polynucleotide array; code that receives as input reference nucleotide sequences from a plurality of members'of a gene family; code that identifies a set of features in the polynucleotide array having probes that define the nucleotide sequences; code that receives as input hybridization data from a hybridization reaction between a target nucleic acid molecule and polynucleotide probes in the polynucleotide array; code that processes the hybridization data to determine whether the target nucleic acid molecule has a sequence from any of the reference sequences; and a computer readable medium that stores the codes.

In another aspect, this invention provides a method that involves determining whether a target nucleic acid molecule comprises a sequence from one of a set of genes. The method comprises: providing a target nucleic acid molecule comprising nucleotide sequences from genomic DNA; providing a polynucleotide array comprising, for each gene in the set, polynucleotide probes that define at least one sequence signature from a unique region of the gene; generating hybridization data by performing a hybridization reaction between the target nucleic acid molecule and the probes in the sets and detecting hybridization between the target nucleic acid molecule and each of the probes in the sets; and processing the hybridization data to determine whether the target nucleic acid comprises a sequence from the unique region of one of the genes. In one embodiment, the step of processing is performed by a programmable digital computer. In another embodiment, the unique region of the gene codes for an amino acid sequence. In a further embodiment, the polynucleotide array further comprises, for each of the unique regions, a set of polynucleotide probes whose sequences define the degenerate set of nucleotide sequences that encode the amino acid sequence. The probes in such embodiments can in addition or as an alternative comprise sequences that contain generic bases such as inosine particularly at the third codon position. As an even further additional or alternative option, polynucleotide probes can have a mixture of A,C,T, and G in the third codon position within a single feature of a polynucleotide array.

In another aspect, this invention provides a computer program product for analyzing hybridization data comprising: code that receives as input the sequence of a polynucleotide probe in each feature of a polynucleotide array; code that receives as input sequence signatures from a unique region of a plurality of genes; code that identifies a set of features in the polynucleotide array having probes that define the sequence; code that receives as input hybridization data from a hybridization reaction between a target nucleic acid molecule and polynucleotide probes in the polynucleotide array; code that processes the hybridization data to determine whether the target nucleic acid molecule comprises a sequence from any of the sequence signatures; and a computer readable medium that stores the codes.

BRIEF DESCRIPTION OF THE FIGURES

FIG. 1A shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve computer programs including code incorporating the present invention. Although a CD-ROM 17 is shown as the computer readable storage medium, other computer readable storage media including floppy disks, DRAM, hard drives, flash tape memory, tape, and the like may be utilized. Cabinet 7 also houses familiar computer components (not shown) such as a processor, memory, and the like.

Figure 1A:
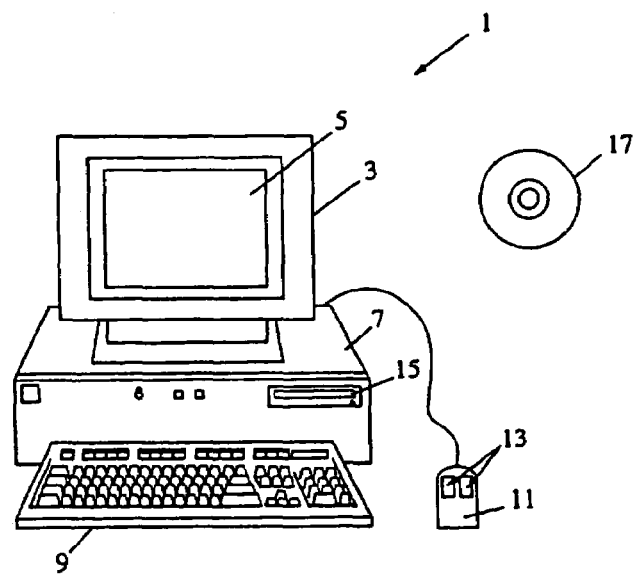
FIG. 1A illustrates an example of a computer system used to execute software that can be used to analyze data generated by the present invention.
Figure 1B:
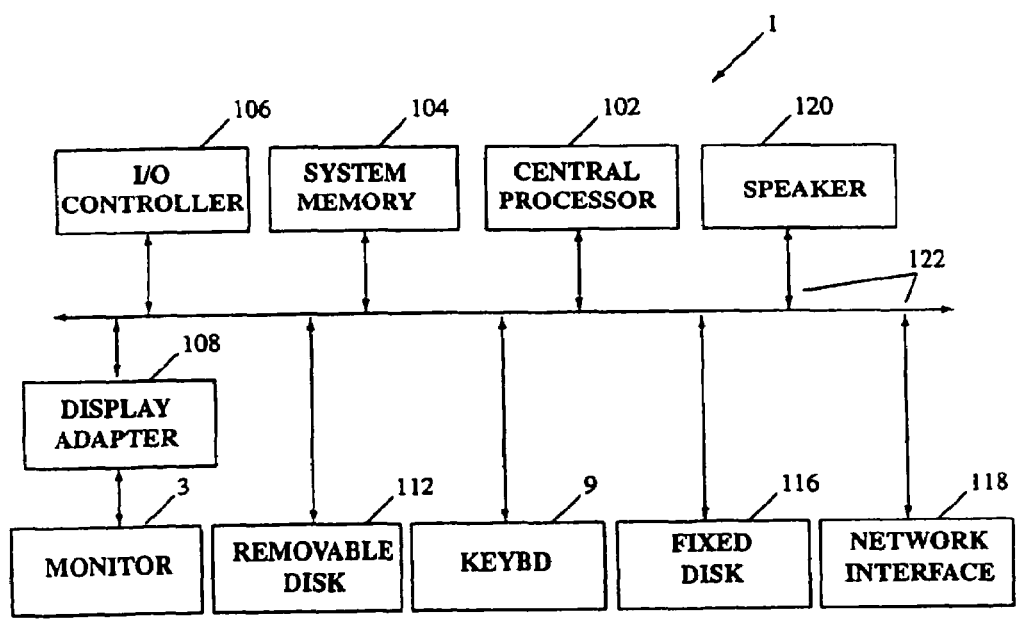
FIG. 1B shows a system block diagram of computer system 1 used to execute software that can be used to analyze data generated by the present invention. As in FIG.

1A, computer system 1 includes monitor 3 and keyboard 9. Computer system 1 further includes subsystems such as a central processor 102, system memory 104, I/O controller 106, display adapter 108, removable disk 112, fixed disk 116, network interface 118, and speaker 120. Removable disk 112 is representative of removable computer readable media like floppies, tape, CD-ROM, removable hard drive, flash memory, and the like. Fixed disk 116 is representative of an internal hard drive, DRAM, or the like. Other computer systems suitable for use with the present invention may include additional or fewer subsystems. For example, another computer system could include more than one processor 102 (i.e., a multi-processor system) or memory cache.

Figure 2:
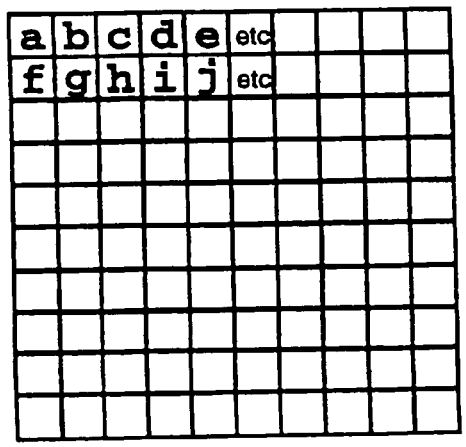

FIG. 2 depicts tiling to detect signature sequence. The signature sequence, Asn-Gly-Lys-Ala-Met (SEQ ID NO:2), encompasses a degenerate set of 64 nucleotide sequences that encode it. One of these is ATTGGCAAAG CTATG (SEQ ID NO:1). A probe set of 6-mers based on single-increment tiling that defines this reference sequence is the set ATTGGC (1-6 of SEQ ID NO:1), TTGGCA (2-7 of SEQ ID NO:1), TGGCAA (3-8 of SEQ ID NO:1), GGCAAA (4-9 of SEQ ID NO:1), GCAAAG (5-10 of SEQ ID NO:1), CAAAGC (6-11 of SEQ ID NO:1), AAAGCT (7-12 of SEQ ID NO:1), AAGCTA (8-13 of SEQ ID NO:1), AGCTAT (9-14 of SEQ ID NO:1) and GCTATG (10-15 of SEQ ID NO:1). Another reference sequence within the degenerate is AACGGAAAGG CAATG (SEQ ID NO:3). A probe set of 6-mers based on-single-increment tiling that defines this sequence is AACGGA (1-6 of SEQ ID NO:3), ACGGAA (2-7 of SEQ ID NO:3), CGGAAA (3-8 of SEQ ID NO:3), GGAAAG (4-9 of SEQ ID NO:3), GAAAGG (5-10 of SEQ ID NO:3), AAAGGC (6-11 of SEQ ID NO:3), AAGGCA (7-12 of SEQ ID NO:3), AGGCAA (8-13 of SEQ ID NO:3), GGCAAT (9-14 of SEQ ID NO:3), and GCAATG (10-15 of SEQ ID NO:3).

Figure 3:
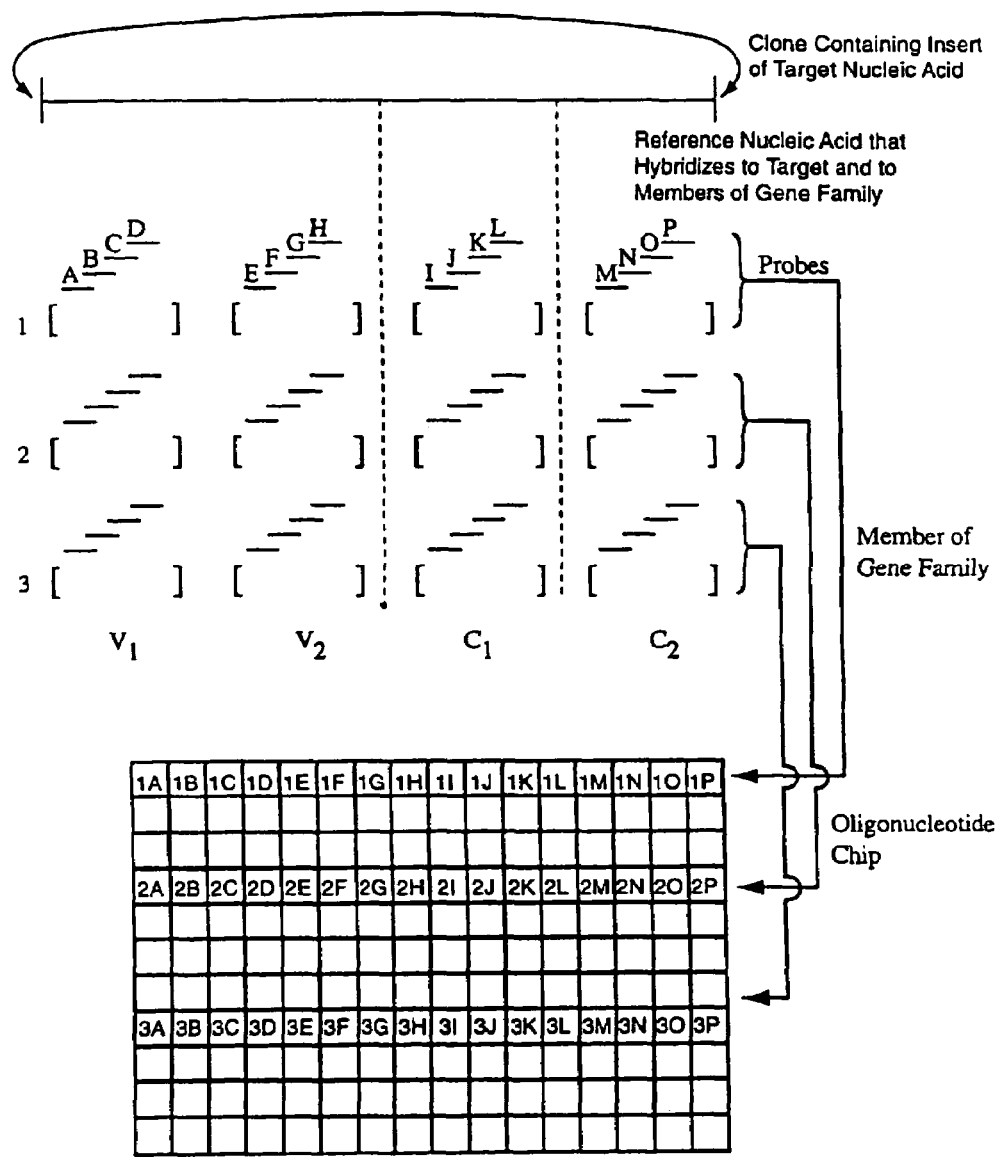

FIG. 3 depicts an example of a strategy for detecting members of a gene family. Four regions of three genes in a family are selected as signature sequences (in brackets). The nucleotide sequence signatures of each of genes 1, 2 and 3 are defined by probe sets that include probes A, B, C, D (variable region $V_1$); E, F, G, H (variable region $V_2$), I, J, K, L (constant region $C_1$) and M, N, O, P (constant region $C_2$).

Figure 4:
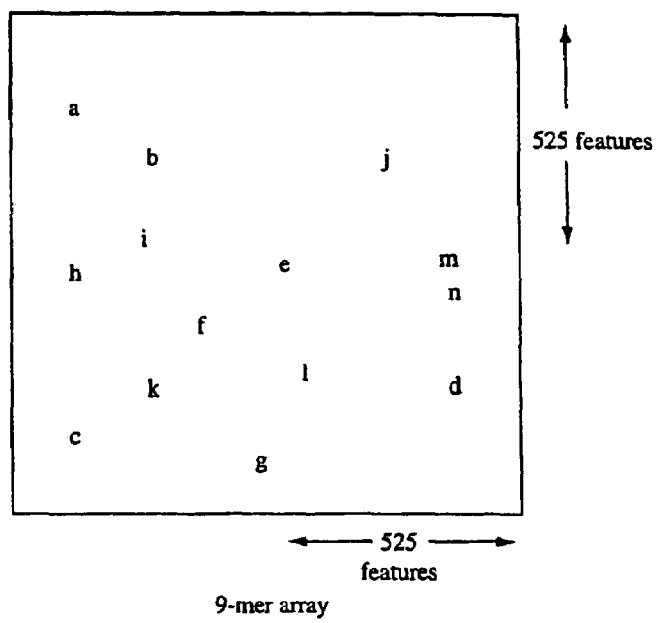

FIG. 4 depicts an example of a strategy for detecting sequence signatures from a variety of genes. In this example, a polynucleotide array having 525×525 features is provided that contains probes with all possible 9-mer sequences. Two polypeptide signature sequences are checked, Asn-Gly-Lys-Ala-Met (SEQ ID NO:2) and Arg-Arg-Gly-Ser-Phe (SEQ ID NO:4) (a site recognized by protein kinase A). Particular nucleotide reference sequences ATTGGCAAAG CTATG (SEQ ID NO:1) and CGCCGCGGAA GTTTT (SEQ ID NO:5) are defined by the probe sets a-g and h-n, respectively. The programmable digital computer contains code that identifies the location on the array of the features having the defining probes, indicated as letters on the array. In processing the hybridization information, it uses data from the features for the defining sets.

Figure 5:
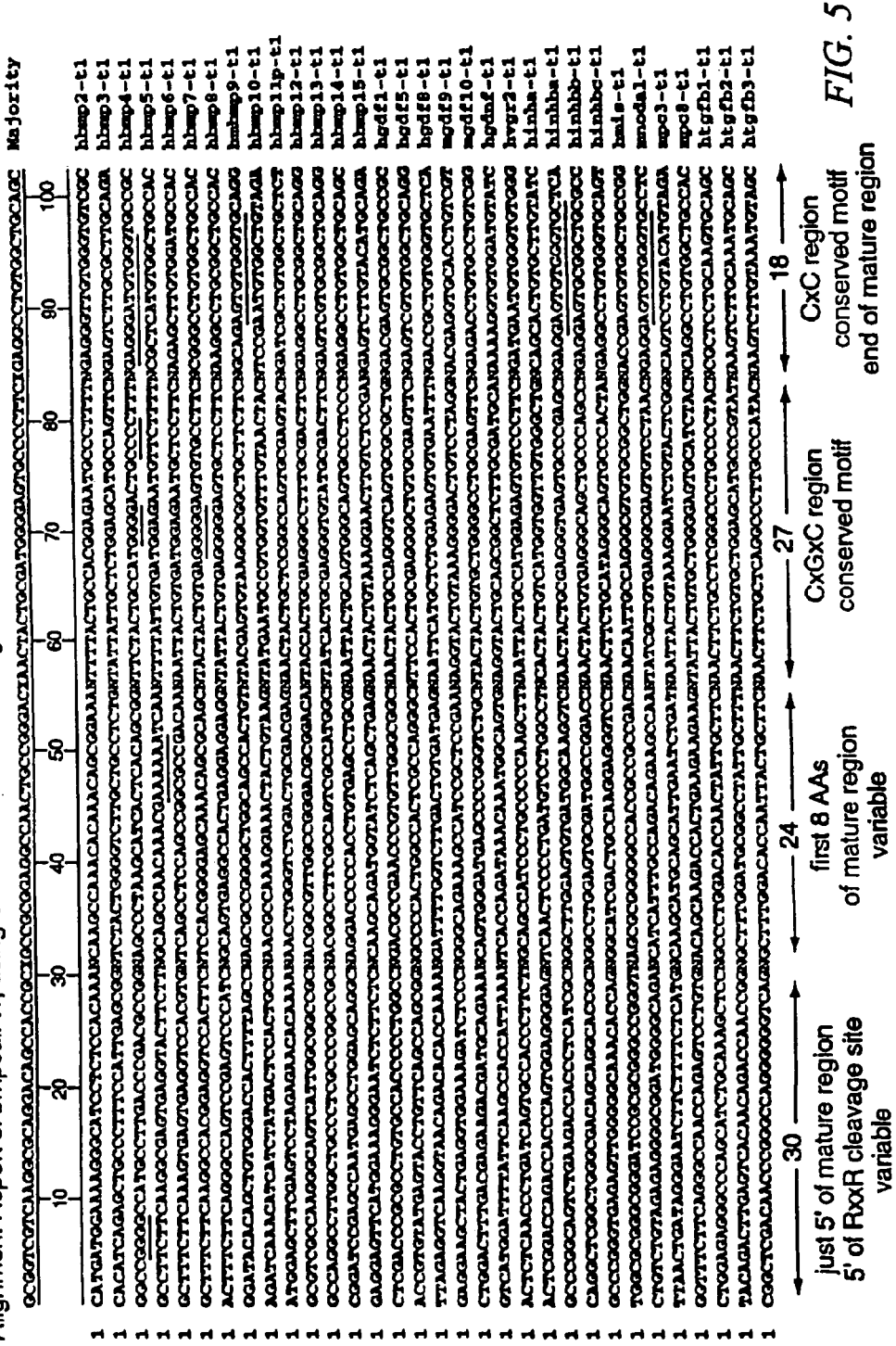

FIG. 5 depicts the nucleotide sequences of four regions of each of thirty-two members of the TGF-β family of genes. (SEQ ID NOS:6-38.) The first region of thirty nucleotides is selected from a variable region just 5' of the mature region of the RXXR cleavage site. The second region of twenty-four nucleotides is a variable region selected from nucleotides encoding the first eight amino acids of the mature TGF-β polypeptide. The third region of twenty-seven nucleotides is selected from the region encoding the CXGXC sequence signature. The fourth region of eighteen nucleotides is selected from the region encoding the CXC conserved motif at the end of the mature coding region of TGF-β. The far right column indicates the clone name from which the sequences were selected.

Figure 6:
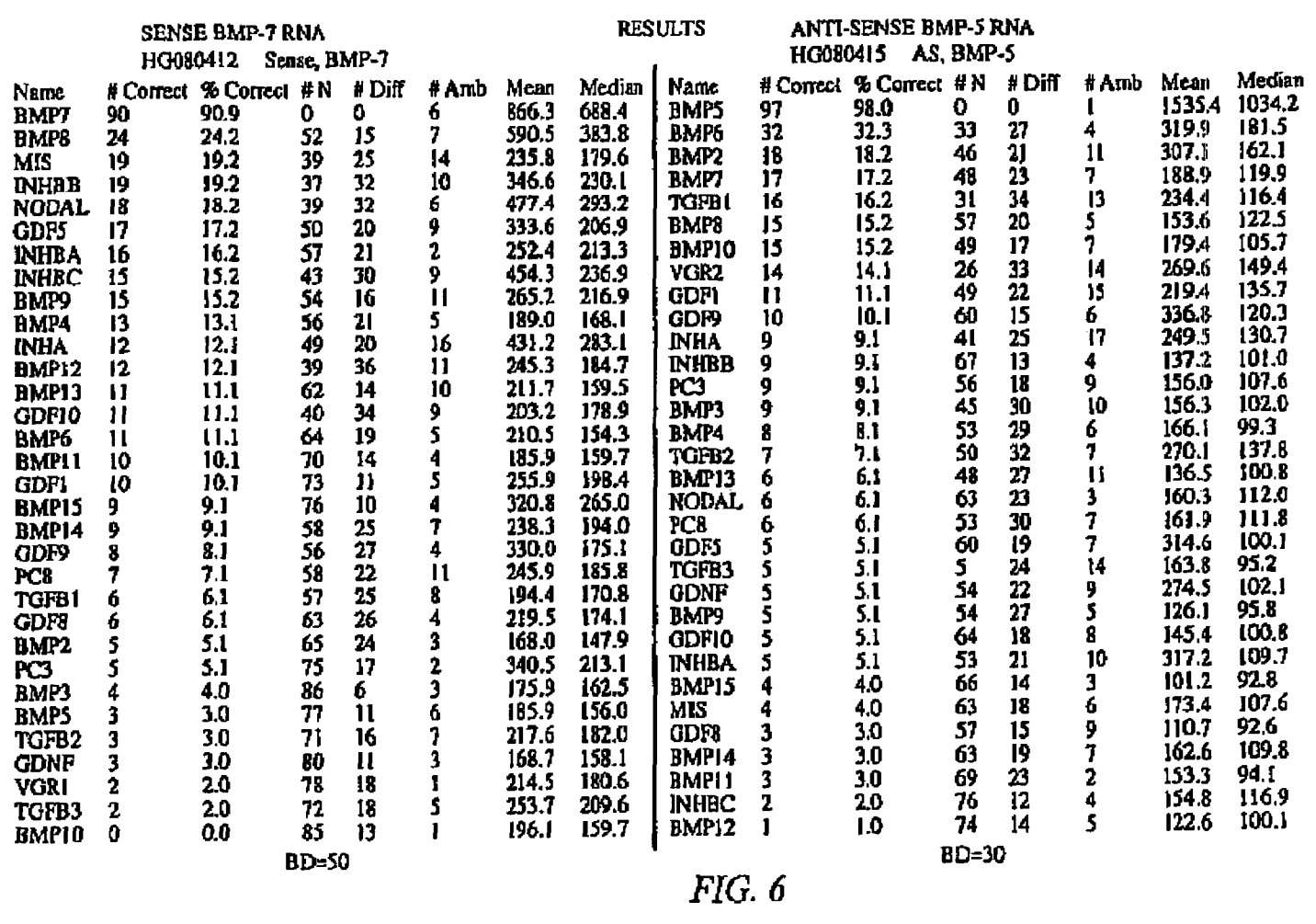

FIG. 6 shows results of a hybridization assay between DNA from TGF-β clones hBMP-7 and hBMP-5 and an array tiled with the sequences described in FIG. 5 using single-increment and trellis tiling for all ninety-nine bases in the four sequence regions of each of the thirty-two TGF-β clones.

DETAILED DESCRIPTION OF THE INVENTION

I. Definitions

As used herein, the following terms have the following meanings.

The term "complementary" refers to the topological compatibility or matching together of interacting surfaces of a probe molecule and its target. Thus, the target and its probe can be described as complementary, and furthermore, the contact surface characteristics are complementary to each other. Complementary includes base complementary such as G is complementary to C and A is the complement of T or U in the genetic code. Complementary also includes other forms of ligand-receptor (also known as ligand-anti-ligand) interactions, such as between other types of receptors and their agonists, antagonists, and other molecules that bind thereto or show some affinity therefor.

The term "probe" includes a surface-immobilized polynucleotide or other polymer that can be recognized by a particular target. Depending on context, the term "probe" refers both to individual polynucleotide molecules and to the collection of same-sequence polynucleotide molecules surface-immobilized at a discrete physical location. Probe and target are often used interchangeably depending upon the context; a probe can bind or become associated with a target as part of a ligand-anti-ligand pair. The probes and targets of the present invention can comprise the nucleic acid bases as found in nature or analogs thereof.

The term "target" refers to a molecule of interest. The probe is useful in obtaining information about the target: whether the target has an affinity for a given probe. Targets may be naturally-occurring or man-made nucleic acid molecules. Also, they can be employed in their unaltered state or as aggregates with other species. Targets may be associated, covalently or noncovalently, to a binding member, either directly or via a specific binding substance. Targets are sometimes referred to in the art as anti-probes. A "Probe-Target Pair" is formed when two macromolecules have combined through molecular recognition to form a complex.

A target molecule can hybridize to a probe set derived from a reference sequence which is complementary to that of the target. Therefor, the sequence of the probe (and the reference sequence) will be the complement of the sequence of the target molecule. Under certain conditions, a target molecule may also hybridize to a probe set defining a reference sequence which is partially complementary to that of the target. However, for ease of comparison, the same sequence will be used to represent a target and the probe and/or reference sequence to which it will hybridize.

The term "feature" refers to an area of a substrate having a collection of substantially same-sequence, surface-immobilized polynucleotide probes. Generally, one feature is different than another feature if the probes of the different features have substantially different nucleotide sequences. Certain features, however, can be designed to have mixtures of sequences for example to query the 3 position of a codon sequence. In the context of light-directed polynucleotide synthesis, for example, a feature is a spatially-addressable synthesis site. See U.S. Pat. Nos. 5,384,261; 5,143,854; 5,510,270; 5,593,139; 5,634,734; and WO/95/11995.

The term "polynucleotide array" refers to a substrate having polynucleotide probes with different, known sequences, at discrete, known locations associated with its surface. Polynucleotide arrays have at least two different features and a density of at least five hundred features per square cm. In certain embodiments the arrays can have a density of about 625, at least one thousand, at least 10 thousand, at least 100 thousand, at least one million or at least 10 million features per square cm. The substrate can be, merely by way of example, silicon or glass and can have the thickness of a glass microscope slide or a glass cover slip. Substrates that are transparent to light are useful when the method of performing an assay on the chip involves optical detection. The term also refers to a probe array and the substrate to which it is attached that form part of a wafer.

"High-density polynucleotide arrays" contain at least 400 different polynucleotide sequences per $cm^2$.

To "screen" means to analyze a sample or target for certain characteristics. One often screens samples to narrow the pool of material that is subjected to further analysis. The assay utilized to screen will be a function of the characteristic that one wants to identify. For example, one can screen using any of the following illustrative methods: immunological methods such as antibody assays, functional assays to see if a starting material exhibits a biological property such as enzyme activity or activity associated with certain cell types, hybridization assays, chemical assays, NMR, mass spectroscopy, chromatography, electron spin resonance, isoelectric focusing, electrophoresis, and the like. Useful screening assays include combinations of these methods performed sequentially or at the same time. It will be apparent to those skilled in the arts that Northern, Southern, and Western blotting and various other methods including but not limited to PCR-based screens, ligation-reaction-based screens, hybridization based screens, size based screens, or affinity-based screens can be employed.

The term "pre-screen" means a screening step that takes place before another step. As used herein, the terms screen and pre-screen can at times be used interchangeably.

The term "sequence" refers, depending on context, to the nucleotide (base) sequence of a nucleic acid or the amino acid sequence of a polypeptide.

The term "nucleic acid sequence signature" refers to a chosen or reference nucleotide sequence. Sequence signatures include nucleotide sequences at most 300, 250, 200, 150, 100, 75, 50, 30, 25 or at most 15 nucleotides in length. Sequence signatures include sequences less than 10, 15, 25, 30, 35, 45, 50, 60, 70, 80, 90, 100, 120, 135, 150, 175, 200, 250 and 300 nucleotides long. Sequence signatures also include any combination of these parameters. Nonlimiting examples of nucleic acid sequence signatures occurring in nature include, e.g., the Hogness Box, the TATA box, a homeobox, the CAAT box and Alu repeat sequences.

The term "polypeptide sequence signature" refers to an amino acid sequence. Amino acids in the sequence signature are selected from the group of twenty common amino acids and also include the less common amino acids. The collection of all amino acid sequences defined by the sequence signature is referred to as the polypeptide "signature set."

Polypeptide sequence signatures include amino acid sequences in which the identity of all, a majority or at least two of the amino acids (common amino acids, uncommon amino acids, or analogues thereof) is fixed. A sequence signature can be chosen to be fixed or variable. Sequence signatures also include amino acid sequences in which the set of amino acids that can occupy a variable position is selected from at most 15, at most 10, at most 5 or at most 2 of the twenty common amino acids. Other amino acids, including those known to those skilled in the biochemical arts as the less common amino acids, are also included. Polypeptide sequence signatures also include amino acid sequences being at most 300, 250, 200, 175, 150, 100, at most 50, at most 10 or at most 5 amino acids in length. Polypeptide sequence signatures also include sequences less than 275, 225, 180, 140, 120, 100, 90, 800,70,50,40,30,20, 10, or 5 amino acids in length. Polypeptide sequence signatures also include any combination of these parameters. Examples of polypeptide sequence signatures include the zinc finger motif and other structural motifs including without limitation coils, loops, helices, turns, leucine zippers, symmetric dimer features, and combinations thereof; the consensus recognition sequence for protein kinase A, for beta globins, for immunoglobulins, for the TGF beta super-family, for DNA binding proteins, steroid-hormone receptor superfamily, to name a few.

The term "gene" refers to a genomic nucleic acid sequence at a particular genetic locus whose exons encode a polypeptide.

The term "region" when referring to a gene, means a sub-sequence of at least 9 contiguous nucleotides within the nucleotide sequence of the gene or a sub-sequence of at least 3 amino acids within the amino acid sequence of a polypeptide encoded by a gene.

The term "unique region" refers to a sub-sequence that is not substantially shared by two genes.

The term "gene family" refers to a collection of genes encoding at least one polypeptide domain whose amino acid sequences have at least 25% sequence identity over a comparison window of at least 20 amino acids. Such domains are related through common ancestry as a result of gene duplication or evolution. Many polypeptide domains are known in the art including, for example, the EGF domain, the immunoglobulin domain, the fibronectin type III domain, the cadherin-like domain, death effector domains (DED) to name a few. See, Vaux, D. L., *Cell, Vol.* 90, pp.389-390 (1997) and in its entirety; *Molecular Biology of the Cell*, 3rd Ed., Alberts et al., (1994). Protein domains are also discussed in more detail in R. F. Doolittle, *Annu. Rev. Biochem.*, (1995) 64:287-314.

Gene families frequently encode polypeptides sharing at least one highly conserved region. Two polypeptides share a "highly conserved region" if the polypeptides have a sequence identity of at least 60% over a comparison window of five amino acids, or if they share a sequence identity of at least 50% over a comparison window of ten amino acids.

Polypeptide members encoded by a gene family, the protein family, can have highly variable regions. A "highly variable region" of a polypeptide encoded by a gene family member is a region of ten amino acids that has less than 30% sequence identity with the same region of a polypeptide of another gene family member. Protein families that can be interrogated using the present invention include the TNF family, the BCL-2 family, actins, the heat shock proteins, keratins, myosin, protein kinases, transcription factors, tubulins, egg shell proteins, alpha globin, beta-like globins, immunoglobulins, ovalbumin, transplantation antigens, visual pigment protein, and vitellogenin as non-limiting examples. See, Vaux, D. L., *Cell*, Vol. 90, pp.389-390 (1997) and in its entirety; *Molecular Biology of the Cell,* 3rd Ed., Alberts et al., (1994); Avise, J. C., *Molecular Markers, Natural History and Evolution*, Chapman and Hall publishers (1994); Stryer, L., *Biochemistry,* 3rd. Ed. (1988); and Atassi, M. Z., *Molecular Immunology*, Marcel Dekker, Inc. (1984).

"Pseudogenes" are-genomic regions that do not result in protein products in the organisms that contain them. Pseudogenes have sequence similarities to their true gene counterparts. Pseudogenes may arise from duplication of ancestral genes except that mutations contained in or near the pseudogene interfere with transcription or translation. Lodish et al., *Molecular Cell Biology,* 3rd. Ed, Scientific American, Inc., New York, N.Y. (1995). As used herein, pseudogenes can be members of gene and protein families that contain their functional counterparts.

"Tandem repeat genes" or "tandemly repeated genes" encode identical or nearly identical proteins or functional RNAs. The copies can appear one after the other separated by spacer regions that can vary within an individual. Lodish et al., *Molecular Cell Biology,* 3rd. Ed, Scientific American, Inc., New York, N.Y. (1995). As used herein the tandem repeat genes are a subset of members of a gene family.

"Tandem repeats" unlike tandem repeat genes can be simply nucleic acids segments that are repeated but do not necessarily encode protein or functional RNAs. These too are subsets of gene families as that term is used herein.

"Simple-Sequence DNA" is largely composed of 5-10 base pair sequences repeated in long tandem repeats. Those skilled in the art will appreciate that simple-sequence DNA is often concentrated at certain regions of a chromosome. For example, a large amount of mouse simple sequence DNA is located near centromers. Accordingly, such sequences can be used as markers and to localize specific chromosomal sites. Lodish et al., *Molecular Cell Biology,* 3rd. Ed, Scientific American, Inc., N.Y., N.Y. (1995).

"Intermediate repeat DNA" or moderately repeated DNA is dispersed throughout various genomes: those of mammals, *drosophila*, and yeast for example. Certain intermediate repeat sequences are transposable DNA elements. Lodish et al., *Molecular Cell Biology,* 3rd. Ed, Scientific American, Inc., New York, N.Y. (1995).

"Spacer DNA" has no currently known function other than to separate functional DNA seuquences. Lodish et al., *Molecular Cell Biology,* 3rd. Ed, Scientific American, Inc., New York, N.Y. (1995).

A polynucleotide probe has a sequence "selected from" a reference sequence if the sequence of the polynucleotide probe is a sub-sequence of the reference sequence. For example, the probe ATTGGC (1-6 of SEQ ID NO:1) has a sequence selected from ATTGGCAAAG CTATG (SEQ ID NO:1).

A set of polynucleotide probes "define" a reference sequence if the sequences of the polynucleotide probes are selected from the reference sequence and if, taken together, the sequences of the polynucleotide probes include the entire sequence of the reference sequence. A probe set also defines sub-sequences within it. For example, the probes ATTGGC and GGCAAA also define the sub-sequence TTGGCA.

The term "tiling strategy" refers to criteria used to select a probe set that defines a reference sequence or set of reference sequences.

"Block tiling" generally refers to a tiling strategy including a set of probes defining a reference sequence in which none of the probes in the set overlap in sequence. For example, the reference sequence ATTGGCAAAG CTATG (SEQ ID NO:1) can be block tiled by the set, ATTGG (1-5 of SEQ ID NO:1), CAAAG (6-10 of SEQ ID NO:1), and CTATG (11-15 of SEQ ID NO:1).

"Single-increment tiling" refers to a tiling strategy including a set of probes that defines a reference sequence in which each probe in the set overlaps in sequence with another probe in the set except for a terminal nucleotide. For example, the reference sequence ATTGGCAAAG CTATG (SEQ ID NO:1) can be single-increment tiled by the set ATTGGC (1-6 of SEQ ID NO:1), TTGGCA (2-7 of SEQ ID NO:1), TGGCAA (3-8 of SEQ ID NO:1), GGCAAA (4-9 of SEQ ID NO:1), GCAAAG (5-10 of SEQ ID NO:1), CAAAGC (6-11 of SEQ ID NO:1), AAAGCT (7-12 of SEQ ID NO:1), AAGCTA (8-13 of SEQ ID NO:1), AGCTAT (9-14 of SEQ ID NO:1) and GCTATG (10-15 of SEQ ID NO:1).

"Double-increment tiling" refers to a tiling strategy including a set of probes that defines a reference sequence in which each probe in the set overlaps in sequence with another probe in the set except for two, consecutive terminal nucleotides. For example, the reference sequence ATTGGCAAAG CTATG (SEQ ID NO:1) can be double-increment tiled by the set ATTGGC (1-6 of SEQ ID NO:1), TGGCAA (3-8 of SEQ ID NO:1), GCAAAG (5-10 of SEQ ID NO:1), AAAGCT (7-12 of SEQ ID NO:1), AGCTAT (9-14 of SEQ ID NO:1) and CTATG (11-15 of SEQ ID NO:1).

"Standard tiling" refers to a tiling strategy for a sub-sequence of a reference sequence. Standard tiling includes a set of probes as follows. All nucleotide positions in the sub-sequence are designated fixed, except for one, which is designated variable. One probe in the set has (or complements) the sequence of the reference sub-sequence. The other probes in the set have the same nucleotide as the reference sub-sequence at the fixed position, but have a different nucleotide at the variable position, and no two probes in the set have the same sequence. Thus, for example, the reference sequence ATTGGCA (1-7 of SEQ ID NO:1) may be standard tiled with the set ATTGGCA (1-7 of SEQ ID NO:1), ATTaGCA, ATTtGCA and ATTcGCA.

"Standard, single-increment tiling" refers to a tiling strategy that combines in a single-increment tiling strategy with a standard tiling strategy for each probe in the single-increment set. For example, the reference sequence ATTGCAAA (1-9 of SEQ ID NO:1) can be tiled with a standard, single-increment strategy with the following probe sets:

```
Reference:      ATTGGCAAA    (1-9 of SEQ ID NO:1)

Probes:   (1)   ATTGGCA,     (1-7 of SEQ ID NO:1)
                ATTaGCA,
                ATTtGCA,
                ATTcGCA;
          (2)   TTGGCAA      (2-8 of SEQ ID NO:1)
                TTGaCAA,
                TTGtCAA,
                TTGcCAA;     and
          (3)   TGGCAAA,     (3-9 of SEQ ID NO:1)
                TGGaAAA,
```

-continued

TGGtAAA,

TGGgAAA.

Hybridization data derived from arrays including standard, single-increment tiling for a reference sequence is useful in base-calling—the determination that a base in a target is different than the base in the reference sequence, and the identification of that different base.

The tiling strategy can be carried out by placing probes in adjacent features on the array. For example, probes defining a sequence in single-increment tiling can be placed in a horizontal row in adjacent features on the array; and probe sets for standard tiling for each of the probes in the single-increment set can be placed in a vertical row beneath the reference sequence.

However, the power of a programmable digital computer can reduce or eliminate the need for customized tiling. For example, a probe array can contain probes defining all possible polynucleotide 9-mers. The computer can carry in its memory the location of the feature containing the probe having any given 9-mer sequence. Then, relying on the reference sequence, the computer can identify the locations of all the probes that make up, for example, the single-increment tiling set for the reference sequence. Similarly, the computer can identify the location of all the probes making up the standard tiling set for each of the probes defining the reference sequence. Then, in processing hybridization data, the computer can be programmed to examine hybridization between target and probe at each of the feature locations defining the single-increment, standard tiling set.

The term "degenerate set" refers to the set of all nucleotide sequences that encode a particular polypeptide sequence signature.

The term "high discrimination hybridization conditions" refers to hybridization conditions in which a single base mismatch can be determined.

Stringency conditions useful in the practice of the present invention are set forth in Sambrook et al., Molecular Cloning: A Laboratory Manual, 2d Ed. (1989).

"Base calling" refers to a process involving comparing the nucleotide sequence of a target molecule with a reference nucleotide sequence and identifying positions at which the nucleotide in the target molecule is different than the nucleotide in the reference sequence. "ID base calling" refers to the process of base calling further involving determining the identity of a nucleotide in the target molecule that is different than a nucleotide in the same position of the reference sequence.

A target nucleic acid sequence is of "unknown genetic origin" if it has not been identified to derive from a known genetic locus.

II. Description

Nucleic acid arrays have been used to interrogate single nucleotide differences between reference and target nucleic acid sequences. The present invention by contrast involves a hierarchical method of array-based analysis in which single nucleotide base determination may or may not be one step. For example, the present invention provides as a first step (or series of steps) the determination of whether a target nucleic acid contains a sequence signature. The sequence signature can comprise, for example, a set of repeat sequences, a conserved region among gene family members, or other multinucleotide groupings that are of interest. The possible outcomes are that a target contains the exact sequence signature in its entirety, lacks the sequence signature in its entirety, or contains one or more variations of the sequence signature. Those outcomes can be used for a variety of purposes: to set up a classification system for nucleic acids of interest based upon sequence signatures, to assign nucleic acids to known groupings of existing classification systems, to determine what if any further analysis is desired, to decide whether to retain or discard all or portions of a nucleic acid sample, and whether special storage or disposal methods are required.

One skilled in the art will appreciate that such outcomes are particularly relevant to diagnosis of patients and in the identification of disease. For example, one can first determine whether a sequence signature present in a possible pathogen or set of pathogens is present in nucleic acids obtained from a patient's body fluids or tissue as a first step in narrowing down a diagnosis. For example, one can determine whether a sequence signature of a mycobacterium is present. See PCT application Ser. No. PCT/US92/02102 (published Aug. 14,1997, publication No. WO97/29212). Using the methods taught in PCT/US92/02102, one can identify, for example, the presence of different mycobacterium species based on sequences signatures. Using the hierarchical methods of the present invention, if no mycobacterium is present, the presence of another suspected pathogen is explored.

The process can be repeated using different arrays having different sets of sequence signatures until the desired level of detail regarding the sequence of the target nucleic acid is obtained. Alternatively, this multistep process can be carried out in a single experiment on one array having probes directed to multiple sequence signatures. The methods disclosed herein can also be employed using one or more arrays in serial or parallel fashion.

The present invention relies upon the outcomes of first determinations to make decisions or further determinations until the desired level of information is determined. The present invention also provides a method of probing for the presence or absence of sequence signatures and their variants in a binary or trinary fashion. Binary analysis asks whether a specific sequence signature is identified or not; a binary determination is a yes/no determination. A trinary analysis asks whether a specific sequence signature is present, absent, or whether a variant of that sequence signature is present; a trinary determination is a yes/no/variant determination. One will appreciate that a quaternary analysis can also ask whether a variant is absent, and so on. The hierarchies contemplated by the present invention include a first determination based upon binding of a target to an array followed by at least one other array-based determination of interest.

In binary and trinary analyses in which the goal is novel gene discovery, often the most useful information is contained in those samples that do not contain a particular sequence (a no in both binary and trinary analysis) or those samples that contain a variant of a particular sequence (a variant in trinary analysis). When doing gene discovery, it is of enormous benefit to pre-screen nucleic acids for those that contain a sequence that has already been identified (a yes in binary or trinary analysis). One can, for example, discard all of the samples that contain the known sequence signature to focus further study on only those nucleic acids that do not contain that sequence signature. When looking for new genes, much time, labor, and money is saved by narrowing the pool of samples for analysis using this embodiment of the present invention.

An example of the practice of the present invention involves determining whether a set of samples contains a nucleic acid that is a member of a gene family. As a first step or first series of steps, one can determine the level of hybridization between nucleic acids contained in those samples and arrayed probes that interrogate the sequence of either strand of a DNA encoding at least a portion of a conserved region associated with a gene family of interest. The samples are then divided according to the results. For purposes of illustration, assume that of a set of three patient samples, the nucleic acids derived from those samples showed the presence of the entire portion of the probed for conserved sequence, the absence of the entire portion of the probed-for conserved sequence, and at least one variant of the portion of the probed-for conserved sequence. The patient samples and/or nucleic acids derived therefrom are segregated or classified accordingly into new sets, 1, 2, and 3. If a greater level of detail regarding one or more of the segregated sets is desired, further analysis is performed. The further analysis can differ for each of the 3 (in this case) sets.

Further inquiry of set 1 can include looking for any remaining portions of the conserved sequence that were not interrogated in the first step(s). Based on the results of such further inquiry, set 1 can be further divided into three subsets: A, B, and C. Those subsets can be analyzed to determine the presence of other conserved sequences or variants thereof. The subsets are further divided into three sub-subsets, for example. The sub-subset can be analyzed for the presence of another sequence signature and so on.

Such an inquiry is particularly useful for identifying new members of gene families. For example, any samples or sets that contain nucleic acids containing sequence signatures that together identify those nucleic acids as member of a gene family can be further screened using arrays that contain probes that query the non-conserved regions of the known gene family members. The arrays can be tiled to permit identification of sequence differences at the single nucleotide level so that the novel sequence of the new family member is obtained.

It will also be appreciated that this method is also beneficial to industries involving large scale manufacture of polymers. In the biotechnical arts, for example, large scale recombinant protein synthesis can result in mixtures of recombinantly produced polypeptides. In certain cases, for example, E. coli can insert so called "friendly" codons under certain fermentation conditions into some but not all of the polypeptide product. One can test recombinant protein for the presence of sequence signature variants as the first step or series of steps in a decision tree. That decision tree can involve the segregation of lots that contain the variants from those that do not. The variant lots can be discarded or further analyzed to the level of detail desired.

It will also be appreciated that the present invention involves the use of an array, preferably a high density array, in a least one of the steps of any method taught herein. The other steps may be performed using techniques known to those skilled in the arts. In addition, this application discusses the invention often in terms of nucleic acid arrays and nucleic acid analysis. Analysis of other materials and the use of other polymer arrays, including without limitation polypeptide and polysaccharide arrays is contemplated by the present invention.

The hierarchy of analysis taught herein confers several advantages. One such advantage is conferred by looking, for example, at a small segment of sequence data—the sequence of the signature or sets of signatures instead of the full length sequence—to determine what if any further analysis is desired. By taking this hierarchical approach, the time, labor, cost, and amount of materials involved in handling and manipulating sample for analysis can be reduced.

The present invention not only provides this novel hierarchy of analysis, it further teaches that for discovery of previously uncharacterized molecules, the most useful information can be derived from analysis of those samples that have been shown to not contain, or segregated after a screening step to decrease the likelihood of containing previously characterized sequence signatures or parts thereof. For example, a sample that contains a sequence signature or a variant from a conserved region of a gene family but does not contain the unique sequence signatures that characterize the different members of that gene family likely contains a novel member of the gene family. In such cases, further analysis of that sample is particularly desirable. For example, in such cases, and at that stage in the hierarchy of analysis, determination of the full length sequence or at least of the region that differs from the unique region of other members of the putative gene family is appropriate. Prior to or simultaneously with determination of the full length sequence at the single nucleotide level, one can obtain the footprint or bar code hybridization pattern. See WO97/29212 and EP Application Ser. No. 95307476.2, filed Oct. 20, 1995, published as EP 0717113A2, Jun. 19, 1996. It will be appreciated that at least in certain circumstances, single nucleotide determination can be inferred from the footprint or other hybridization pattern.

The hierarchical methods of the present invention are particularly useful in the identification of gene family members; the discovery of new gene family members or other molecules; the identification of nucleic acid fragments as being from or containing certain regions of a genome (human or otherwise); the handling or disposal of potentially hazardous materials including without limitation those containing prions or nucleic acid materials such as retroviruses; the segregation of materials into different biohazard groupings; epidemiological characterization and analyses; analysis of recombinantly or enzymatically manufactured biological materials such as nucleic acids (including without limitation antisense agents, ribozymes, promoter sequences, control sequences, restriction site sequences, capped sequences, tailed sequences, branched sequences, methylated sequences, vector sequences, analogues including peptide nucleic acids, and other sequences or varieties) proteins or peptides (including without limitation insulin, growth factors, antibodies, endorphins, enkephalins, and protein or peptide analogues) carbohydrates of all forms and analogues thereof, proteoglycans, and filementious materials including without limitation those containing fibrins, actins, myosin, tropomyosin, troponin, and meromyosin; quality control and assurance for manufactured biological materials, natural or synthetic polymers, or other chemical materials; the narrowing of a clone pool; and others.

All of the methods discussed herein can include: correlating RNA levels with gene sequences of interest; the identification and use of expression patterns; the narrowing of expression pattern information in a hierarchical fashion; or the selection, including by experimental design, of subsets of particular expression profiles. For example, one can look for the absence of sequence signatures of enzymes involved in a particular metabolic pathway. If one or more of the sequence signatures are missing, one may conduct a second assay for the sequence signatures of other enzymes that can or are thought to metabolize the excess accumulation of bioproducts that results from the enzyme deficiency screened for in the first assay.

A. Screening Methods
1. Analyzing for Sequence Signatures

In one aspect, this invention provides methods that involve analyzing a nucleic acid molecule for the presence of a sequence signature. Such analysis involves starting with a polynucleotide array that contains a set of probes that define the sequence signature; generating hybridization data by performing a hybridization assay between the target and the array and detecting hybridization between the target and the probes in the array, and processing the hybridization data to determine whether the target contains the sequence signature.

The probes required on the polynucleotide array depend upon the sequence signature to be analyzed. The sequence signature can be, for example, an amino acid sequence or a nucleotide sequence. The sequence signature could define, for example, a polypeptide domain. The sequence signature could be a fixed sequence or a consensus sequence in which certain of the positions are not fixed. Consider, for example, the consensus recognition sequence for protein kinase A: RRX(S/T)Z, wherein X is any amino acid and Z is a hydrophobic amino acid selected from valine, leucine or isoleucine (SEQ ID NO:3). The signature set for this amino acid sequence comprises 1×1×20×2×3, or 240 different amino acid sequences. The number of nucleotide sequences that encode this signature set equals the product of the number of codons that encode the possible amino acids at each position. In this case, a complete degenerate set for all the amino acid sequences in the signature set contains 6×6×61×(6+4)×(4+6+3)=285,480 different reference nucleotide sequences. In contrast, the degenerate set of all possible nucleotide sequences encoding the single recognition sequence RRGSV (SEQ ID NO:39), is 6×6×4×6×4=3456 sequences. For recognition of certain sequence signatures, a generic array of all possible 8-mers, for examples, can be particularly useful. See PCT application Ser. No. 97US/01603, filed Jan. 22, 1997, PCT publication No. Wo97/17317.

In one embodiment, a polynucleotide array is selected that contains probe sets defining the complete degenerate set of nucleotide sequences encoding all possible amino acids in the amino acid signature sequence. However, alternative approaches are possible, depending upon the particular sort of analysis one wishes to undertake. For example, one might wish to analyze only a sub-set of the amino acid sequences in the polypeptide signature set. In this case, one can select a polynucleotide array whose probe sets define the degenerate sets encoding only those amino acid sequences. Or, one may wish to screen for targets having selected codons encoding all or some of the amino acids in the polypeptide signature set. In this case, one can select a polynucleotide array having probe sets that define less than the degenerate set for any particular amino acid sequence, e.g., at least 25%, at least 50%, at least 75% or at least 95% of the degenerate set of sequences encoding the polypeptide sequence signature. (See FIG. 2.) Combinations of the two approaches are also possible. Useful probe sets can also contain generic bases such as inosine or mixtures of A, C, T, G, or U at the equivalent of the third codon position in the sequence.

One then carries out a hybridization reaction in which the target nucleic acid sequence is contacted with the polynucleotide probe under hybridization conditions. If the target nucleic acid molecule is very long, one can optionally break the target into fragments and contact the array with the fragments. Usually the target or fragments thereof are detectably labeled so that the positions at which they have hybridized can be determined.

After carrying out the hybridization reaction, hybridization is detected between selected probes and the target to generate hybridization data. This data usually reflects the amount of hybridization, as determined by the strength of the detectable signal (fluorescence for example), between the target and the probes at a particular feature. One can use high, intermediate, or low discrimination hybridization conditions as desired.

The hybridization data is then processed, preferably by programmable digital computer, to determine whether the target contains a nucleotide reference sequence defined by any probe set. Processing the hybridization information can comprise determining the degree of fidelity of hybridization between the target nucleic acid molecule and each probe in the set, whereby hybridization with high fidelity to all the probes in the set indicates that the target nucleic acid molecule contains the sequence signature, and hybridization with high fidelity to a subset of the probes in the set indicates that the target nucleic acid molecule has part of the sequence signature.

For example, suppose one desired to determine whether a target polynucleotide encoded the amino acid sequence RRGSV (SEQ ID NO:39). As stated above, 3456 nucleotide sequences encode this amino acid sequence. An array can be selected that includes probe sets using a single-increment tiling strategy defining the degenerate set of nucleotide sequences that encodes RRGSV (SEQ ID NO:39). Suppose, further, that the target nucleic acid has the sequence CGACGAGGGTCTGTC (SEQ ID NO:40), which encodes RRGSV (SEQ ID NO:39). Under high discrimination hybridization conditions, this target sequence would hybridize to the single-increment probe set as depicted by asterisk:

```
Signature:      R R S V G            (SEQ ID NO:39)

Reference:      CGACGAGGGTCTGTC      (SEQ ID NO:40)

Probes:         *CGACGA,

*GACGAG,

*ACGAGG,             (SEQ ID NO:58)

*CGAGGG,

*GAGGGT,

*AGGGTC,

*GGGTCT,

*GGTCTG,

*GTCTGT,    and

*TCTGTC.
```

By detecting hybridization between the target and each of the above probes, one can determine that the target molecule has the sequence of the reference sequence. One can also determine a hybridization pattern to identify the sequence signature.

An array that contained probe sets defining all degenerate sequences encoding RRGSV (SEQ ID NO:39) also would contain a probe set defining the sequence CGCCGAGGGTCCGGG (SEQ ID NO:41). It would hybridize to the target molecule as shown with an asterisk:

```
Signature:      R R S V G         (SEQ ID NO:39)
Target:         CGACGAGGGTCTGTC,  (SEQ ID NO:40)
Reference:      CGCCGAGGGTCCGGG,  (SEQ ID NO:41)
Probes:    CGCCGA,
           GCCGAG,
           CCGAGG,
          *CGAGGG,
          *GAGGGT,
          *AGGGTC,
           GGGTCC,
           GGTCCG,
           GTCCGG, and
           TCCGGG.
```

Thus, upon detecting hybridization between the target and this probe set, one can determine that the target does not have this complete reference sequence, or is related to a sequence signature although it encodes the sequence RS.

The target may hybridize to part of a reference nucleotide sequence but it may not hybridize at positions representing particular codons. In this case, the target does not encode the polypeptide sequence signature, but may encode a related sequence signature which varies from the original as a result of a variable amino acid position. If the array contains probes defining sequence signatures that include such variable positions, the computer system can process the hybridization data from the probe sets defining these other sequence signatures, to determine whether the target encodes one of these. If the target fails to hybridize to the probes defining a sequence signature, then the target does not encode this sequence signature.

The array need not include probes defining the degenerate set of nucleotide sequences encoding a polypeptide sequence signature. As an alternative to a degenerate set of nucleotide sequences, one can provide for generic bases such as inosine or mixtures of A, C, T, G, and U at what corresponds to the third codon position. In addition, one can employ footprint, molecular bar-coding, or other hybridization patterns to determine the presence of, absence of, or variance from the reference sequence signature.

In another embodiment of this method, the array further comprises probe sets selected for standard tiling of a reference sequence. Suppose, for example, that as a result of mutation, the target nucleic acid has the sequence CGA CGA tGG TCT GTC (SEQ ID NO:42), which encodes RRWSV (SEQ ID NO:43). A probe set that is standard tiled throughout the reference sequence may include probe sets that hybridize to the target as follows:

```
Signature:   R R S V G          (SEQ ID NO:39)
Reference:   CGACGAGGGTCTGTC    (SEQ ID NO:40)
Target:      CGACGAtGGTCTGTC    (SEQ ID NO:42)
Probes:     *CGACGA,
             CGtCGA,
             CGgCGA,
             CGcCGA,
             GACGAG,
             GAaGAG,
             GAtGAG,
             GAgGAG,
             ACGAGG,
             ACaAGG,
             ACtAGG,
             ACcAGG,
             CGAGGG,
             CGtGGG,
             CGgGGG,
             CGcGGG,
             GAGGGT,
             GAaGGT,
            *GAtGGT,
             GAcGGT,
             AGGGTC,
             AGaGTC,
             AGtGTC,
             AGcGTC,
             GGGTCT,
             GGaTCT,
             GGtTCT,
             GGcTCT,
            *GGTCTG,
             GGaCTG,
             GGgCTG,
             GGcCTG,
            *GTCTGT,
             GTaTGT,
             GTtTGT,
             GTgTGT,
            *TCTGTC,
             TCaGTC,
             TCgGTC,
             TCcGTC.
```

From this information, one can determine that the target does not encode the signature sequence, but has the sequence:

```
    *CGACGA,

*GAtGGT,

*GGTCTG,

*GTCTGT,

*TCTGTC         or

CGACGAtGGTCTGTC,    (SEQ ID NO:42) which encodes

R  R  W  S  V.     (SEQ ID NO:43)
```

Software such as the GeneChip® software from Affymetrix, Inc. (Santa Clara, Calif., USA) can be used to analyze the hybridization data. See also International Publication No. WO 97/28212, European Patent Application Publication No. EP 0717113A2 (European Patent Application No. 95307476.2).

2. Screening for Members of a Gene Family

In another aspect, this invention provides methods for determining whether a target nucleic acid molecule encodes a member of a gene family. This method is useful for determining whether a target molecule is a known member of a family, or a new, previously unknown, member. In selecting arrays for this type of screening, several parameters can be varied.

One parameter is the number of gene family members whose sequences are used on the array. Probe sets defining sequences from at least one and more preferably at least two members of the family are used on the array. However, for the identification of new family members, one preferably creates arrays containing probe sets defining sequences from all known members of the family.

Another parameter that can be varied is the number of sequence signatures from each member of the gene family that are defined by probe sets on the array. A comparison of the amino acid and nucleotide sequences of known members of a gene family reveals both highly conserved and variable sequence regions. Conserved regions, because they share a higher degree of identity between members, are more useful for determining whether a target encodes a member of the family. Variable regions, because they are the most distinct, are more useful for discriminating between members of the family and for indicating whether a target encodes a new member of the family.

Accordingly, arrays used for screening members of a family contain probe sets defining at least one sequence signature from each member of the gene family.

Another parameter that can be varied, related to the second parameter, is the number of nucleotide sequences within a degenerate set encoding an amino acid signature sequence from one or more of the gene family members from which probe sets are chosen. For example, a nucleic acid signature sequence from a member of a gene family, if it is within the coding region of the gene, encodes an amino acid sequence. Probe sets can be selected that define not only the reference nucleotide sequence, but members of the degenerate set that encode the same amino acid sequence as the reference nucleotide sequence. Such probe sets are useful in identifying polymorphisms of any gene family member, as well as new members of the family. Generic bases and probes having mixtures of bases at certain codon positions, such as the third codon position can also be employed.

Another parameter is the length of the sequence signature. While there is no particular size limit, sequence signatures are preferably at least 9 nucleotides long. A collection of sequence signatures totaling between 75 and 125 nucleotides spread among about 4 signatures is particularly useful.

Any nucleic acid molecule can be used as a target molecule in this method. However, often, the target is a molecule that has been pre-screened in accordance with the teachings of the present invention so that there is reason to believe the target may be a member of the gene family. For example, one may screen a DNA library with probes (which can include degenerate sets, generic bases, and mixtures of nucleotides at certain positions) having a sequence-selected from one or more-members of the gene family. Depending upon the stringency of the hybridization conditions used, the probe may hybridize to sequences more closely or more distantly related to the probe. Thus, the target sequence can be one that hybridizes under a selected set of hybridization conditions to a probe having the reference sequence.

The hybridization data generated from a hybridization reaction between the target and the probes on the array is processed to determine whether the data is consistent with the target nucleic acid being a member of the gene family. This can involve, for example, base calling the target sequence over at least a sequence signature for a conserved region of the gene or the determination of whether the overall pattern expected for that sequence signature is present.

The hybridization data may indicate that the target molecule has sequences that are identical to that of a known member of the gene family. However, if the hybridization data indicates that there are differences between the target sequence and the reference sequences, the extent of the differences provides further information about the identity of the target sequence.

For example, if the differences are few enough, their location and identity can in certain embodiments be determined by ID base calling using, e.g., arrays that employ single increment, standard tiling. In this case, the information is consistent with the target being one of the known gene family members, possibly including allelic forms of the gene.

If there are significant differences between the target and the probe sets, then the hybridization is generally quite weak in the regions that differ. In this case, the target is identified as containing an insertion that is not a previously known member of the family. The practitioner then can decide whether the clone is worth sequencing to determine if it is actually a member of the family, and, if so, how it differs from the other members.

3. Screening for Gene Sequences

As we move into a world in which all the genes of the human and other genomes are identified and sequenced, the focus of much nucleic acid analyses will be the identification of which genes are present in a particular sample. Such identification is particularly useful in the hierarchical methods of the present invention. Accordingly, this invention also provides methods of determining whether a target nucleic acid molecule has a nucleotide sequence from any of a set of genes. The methods involve providing an array with probe sets defining sequence signatures from the gene set. Hybridization data is collected from a hybridization reaction between the target and the probes on the array. The data is analyzed to determine whether the target contains the sequence signature of one of the genes in the set.

The hybridization data can be processed in the following manner. The extent of hybridization between the probes that define each sequence signature and the target can be determined. If the target has a sequence closely related to one of the sequence signatures, the degree of hybridization between the target and the probe set that define the sequence signature of that gene will be strong compared to the hybridization signal with other sequence signatures defined in the array. This assists in identifying sequence signatures in the target. Computerized methods for analyzing hybridization data from nucleic acid arrays are taught by WO97/29212; EP publication No. 95307476.2.

Preferably the sequence signatures are unique to the genes in the set. A sequence signature of about 20 nucleotides suffices in most cases to uniquely identify a gene. The signature sequence can be from, for example, a transcribed or coding region of the gene. Such arrays are useful for example for determining the identity of target cDNA molecules, variants of genomic clones.

One can obtain further information about a target sequence by providing arrays with probe sets in single-increment, standard tiling systems for each nucleotide in each of the sequence signatures. In this case, when the target does not perfectly match a sequence signature, differences between the two sequences can be determined by base calling. Alternatively, recognition of the hybridization pattern is employed.

B. Performing Hybridization Assays

Hybridization assays on substrate-bound polynucleotide arrays involve a hybridization step and a detection step. In the hybridization step, a hybridization mixture containing the target and, preferably, a hybridization optimizing agent, such as an isostabilizing agent, denaturing agent or renaturation accelerant, is brought into contact with the probes of the array and incubated at a temperature and for a time appropriate to allow hybridization between the target and any complementary probes. Usually, unbound target molecules are then removed from the array by washing with a wash mixture that does not contain the target, such as hybridization buffer. This leaves only bound target molecules. In the detection step, the probes to which the target has hybridized are identified and the amount hybridized is determined by the intensity of the label. Since the nucleotide sequence of the probes at each feature is known, identifying the locations at which the target has bound provides information about the particular sequences of these targets.

The hybridization mixture includes the target nucleic acid molecule and a hybridization optimizing agent in an appropriate solution, i.e., a hybridization buffer. The target nucleic acid molecule is present in the mixture at a concentration between about 0.005 nM and about 50 nM preferably between about 0.5 nM and 5 nM or, more preferably, about 1 nM and 2 nM. The target nucleic acid molecule preferably includes a detectable label, such as a fluorescent or other type of label which can attach to the bound target (i.e. biotin).

Betaines and lower tetraalkyl ammonium salts are examples of isostabilizing agents. Denaturing agents are compositions that lower the melting temperature of double stranded nucleic acid molecules by interfering with hydrogen bonding between bases in a double-stranded nucleic acid or the hydration of nucleic acid molecules. Denaturing agents include formamide, formaldehyde, DMSO ("dimethylsulfoxide"), tetraethyl acetate, urea, GuSCN, glycerol and chaotropic salts. Hybridization accelerators include heterogenous nuclear ribonucleoprotein ("hnRP") A1 and cationic detergents such as, preferably, CTAB ("cetyltrimethylammonium bromide") and DTAB ("dodecyl trimethylammonium bromide"), and, also, polylysine, spermine., spermidine, single stranded binding protein ("SSB"), phage T4 gene 32 protein and a mixture of ammonium acetate and ethanol.

The hybridization mixture is placed in contact with the array and incubated. Contact can take place in any suitable container, for example, a dish or a cell specially designed to hold the array and to allow introduction of the fluid into and removal of it from the cell so as to contact the array. Generally, incubation will be at temperatures normally used for hybridization of nucleic acids, for example, between about 20° C. and about 75° C., e.g., about 25° C., about 30° C., about 35° C., about 40° C., about 45° C., about 50° C., about 55° C., about 60° C. or about 65° C. For probes longer than about 14 nucleotides, 20° C.-50° C. is preferred. For shorter probes, lower temperatures are preferred. The target is incubated with the probe array for a time sufficient to allow the desired level of hybridization between the target and any complementary probes in the array. Using a hybridization temperature of 25° C. can yield a very clear signal, usually in at least 30 minutes to two hours, but it may be desirable to hybridize longer, i.e., about 15 hours.

After incubation with the hybridization mixture, the array usually is washed with the hybridization buffer, which also can include the hybridization optimizing agent. These agents can be included in the same range of amounts as for the hybridization step, or they can be eliminated altogether. Then the array can be examined to identify the probes to which the target has hybridized.

C. Preparation of Target Samples

The target polynucleotide whose sequence is to be determined can be isolated from a clone, a cDNA, genomic DNA, RNA, cultured cells, or a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually, though not always, reverse transcribed to DNA. DNA samples or cDNA resulting from reverse transcription are usually amplified, e.g., by PCR. Depending on the selection of primers and amplifying enzyme(s), the amplification product can be RNA or DNA. Paired primers are selected to flank the borders of a target polynucleotide of interest. More than one target can be simultaneously amplified by multiplex PCR in which multiple paired primers are employed. If the target is a long polynucleotide, it may be appropriate to fragment the target into smaller pieces before performing the hybridization reaction. As used herein, the detection of hybridization between a target and probes on an array includes performing the hybridization reaction with all or portions of the target.

The target can be labeled at one or more nucleotides during or after amplification. For some target polynucleotides (depending on size of sample), e.g., episomal DNA, sufficient DNA is present in the tissue sample to dispense with the amplification step. Preferred labels include fluorescent labels, chemi-luminescent labels, bio-luminescent labels, and calorimetric labels, among others. Most preferably, the label is a fluorescent label such as a fluorescein, a rhodamine, a polymethine dye derivative, a phosphor, and so forth. Commercially available fluorescent labels include., inter alia, fluorescein phosphoramidites such as Fluoreprime (Pharmacia, Piscataway, N.J.), Fluoredite (Millipore, Bedford, Mass.) and FAM (ABI, Foster City, Calif.).

Useful light scattering labels include large colloids, and especially the metal colloids such as those from gold, selenium, silver, tin, and titanium oxide.

Radioactive labels include, for example, $^{32}P$ This label can be detected by a phosphorimager. Detection, of course, depends on the resolution of the imager. Phosophorimagers are available having resolution of 50 microns. Accordingly, this label is currently useful with chips having features of at least that size.

In one embodiment, biotinylated bases are incorporated into the target nucleic acid. Hybridization is detected by staining with streptavidin-phycoerythrin.

When the target strand is prepared in single-stranded form as in preparation of target RNA, the sense of the strand should of course be complementary to that of the probes on the chip. This is achieved as an example by appropriate selection of primers used for any amplification of the target. Also, the array can contain probes for both strands.

The target is preferably fragmented before application to the chip to reduce or eliminate the formation of secondary structures in the target and reduce any overhang interaction. The average length of the target segments following hybridization is usually longer than the length of the probes on the chip.

D. Substrate-Associated Polynucleotide Arrays

Substrate-associated polynucleotide arrays used in the assays of this invention typically include between about $5 \times 10^2$ and about $10^8$ features per square centimeter, or between about $10^4$ and about $10^7$, or between about $10^5$ and $10^6$.

Preferably, the arrays are produced through spatially directed polynucleotide synthesis. As used herein, "spatially directed polynucleotide synthesis" refers to any method of directing the synthesis of a polynucleotide to a specific location on a substrate. Methods for spatially directed polynucleotide synthesis include, without limitation, light-directed polynucleotide synthesis, microlithography, application by ink jet, microchannel deposition to specific locations and sequestration with physical barriers. In general these methods involve generating active sites, usually by removing protective groups; and coupling to the active site a nucleotide which, itself, optionally has a protected active site if further nucleotide coupling is desired.

In one embodiment substrate-bound polynucleotide arrays are synthesized at specific locations by light-directed polynucleotide synthesis. The pioneering techniques of this method are disclosed in U.S. Pat. No. 5,143,854; PCT WO 92/10092; PCT WO 90/15070; and U.S. application Ser. No. 08/249,188, filed May 24, 1994, Ser. No. 07/624,120, filed Dec. 6, 1990, and Ser. No. 08/082,937, filed Jun. 25, 1993. In a basic strategy of this process, the surface of a solid support modified with linkers and photolabile protecting groups is illuminated through a photolithographic mask, yielding reactive hydroxyl groups in the illuminated regions. A 3'-O-phosphoramidite-activated deoxynucleoside (protected at the 5'-hydroxyl with a photolabile group) is then presented to the surface and coupling occurs at sites that were exposed to light. Following the optional capping of unreacted active sites and oxidation, the substrate is rinsed and the surface is illuminated through a second mask, to expose additional hydroxyl groups for coupling to the linker. A second 5'-protected, 3'-O-phosphoramidite-activated deoxynucleoside (C—X) is presented to the surface. The selective photodeprotection and coupling cycles are repeated until the desired set of products is obtained. Photolabile groups are then optionally removed and the sequence is, thereafter, optionally capped. Side chain protective groups, if present, are also removed. Since photolithography is used, the process can be miniaturized to generate high-density arrays of polynucleotide probes.

This general process can be modified. For example, the nucleotides can be natural nucleotides, chemically modified nucleotides or nucleotide analogs, as long as they have activated hydroxyl groups compatible with the linking chemistry. The protective groups can, themselves, be photolabile. Alternatively, the protective groups can be labile under certain chemical conditions, e.g., acid. In this example, the surface of the solid support can contain a composition that generates acids upon exposure to light. Thus, exposure of a region of the substrate to light generates acids in that region that remove the protective groups in the exposed region. Also, the synthesis method can use 3'-protected 5'-O-phosphoramidite-activated deoxynucleoside. In this case, the polynucleotide is synthesized in the 5' to 3' direction, which results in a free 5' end.

The general process of removing protective groups by exposure to light, coupling nucleotides (optionally competent for further coupling) to the exposed active sites, and optionally capping unreacted sites is referred to herein as "light-directed nucleotide coupling."

Tiling strategies for creating probe arrays adapted for various tasks, such as re-sequencing are described in U.S. patent application Ser. No. 08/510,521, filed Aug. 2, 1995 and International application PCT/US94/12305, filed Oct. 26, 1994.

If desired, the substrate-bound polynucleotide array can be appropriately packaged for use in a chip reader. One such apparatus is disclosed in International Publication No. WO 95/33846.

Probes may be laid out on a polynucleotide array with a specifically defined positional relationship. For example, the probes in the set can be positioned in adjacent features on the array. However, hybridization data from a polynucleotide array normally will be processed by a programmable digital computer. The computer memory can be programmed to remember the sequence of each probe at each feature on the array. Consequently, one may provide a polynucleotide array or set polynucleotide arrays containing all possible sequences of probes of a given length. For example, a chip having 525 by 525, or 275,625, features can contain all nine-mer probes having all possible nucleotide sequences of 9 nucleotides ($4^9 = 262,144$). Using any selected tiling strategy, the programmable computer can identify the set of features containing probes that define any given reference sequence. Then, the computer can be programmed to process hybridization data from the probe set that defines a reference sequence.

E. Detecting Fluorescently Labeled Probes

Determining a signal generated from a detectable label on an array requires a polynucleotide array or chip reader. The nature of the polynucleotide array reader depends-upon the particular type of label attached to the target molecules.

In one embodiment the chip reader comprises a body for immobilizing the polynucleotide array. Excitation radiation, from an excitation source having a first wavelength, passes through excitation optics from below the array. The excitation optics cause the excitation radiation to excite a region of a polynucleotide-array on the substrate. In response, labeled material on the sample emits radiation which has a wavelength that is different from the excitation wavelength. Collection optics, also below the array, then collect the emission from the sample and image it onto a detector. The detector generates a signal proportional to the amount of radiation sensed thereon. The signals can be assembled to represent an image associated with the plurality of regions from which the emission originated.

According to one embodiment, a multi-axis translation stage moves the polynucleotide array in order to position different areas to be scanned, and to allow different locations of an array to be interrogated. As a result, a 2-dimensional image of the polynucleotide array is obtained.

The polynucleotide array reader can include an auto-focusing feature to maintain the sample in the focal plane of the excitation light throughout the scanning process. Further, a temperature controller may be employed to maintain the sample at a specific temperature while it is being scanned. The multi-axis translation stage, temperature controller, auto-focusing feature, and electronics associated with imaging and data collection are managed by an appropriately programmed digital computer.

In one embodiment, a beam is focused onto a spot of about 2 μm in diameter on the surface of the array using, for example, the objective lens of a microscope or other optical means to control beam diameter. (See, e.g., U.S. patent application Ser. No. 08/195,889, filed Feb. 10, 1994).

In another embodiment, fluorescent probes are employed in combination with CCD imaging systems. Details of this method are described in U.S. application Ser. No. 08/301,051, filed Sep. 2, 1994. In many commercially available microplate readers, typically the light source is placed above an array, and a photodiode detector is below the array. For the present methods, the light source can be replaced with a higher power lamp or laser. In one embodiment, the standard absorption geometry is used, but the photodiode detector is replaced with a CCD camera and imaging optics to allow rapid imaging of the array. A series of Raman holographic or notch filters can be used in the optical path to eliminate the excitation light while allowing the emission to pass to the detector. In a variation of this method, a fiber optic imaging bundle is utilized to bring the light to the CCD detector. In another embodiment, the laser is placed below the polynucleotide array and light directed through the transparent wafer or base that forms the bottom of the polynucleotide array. In another embodiment, the CCD array is built into the wafer of the polynucleotide array.

The choice of the CCD array will depend on the number of polynucleotides in each array. If 2500 features of sequence-specific polynucleotides nominally arranged in a square (50×50) are examined, and 6 lines in each feature are sampled to obtain a good image, then a CCD array of 300×300 pixels is desirable in this area. However, if an individual array has 48,400 features (220×220) then a CCD array with 1320×1320 pixels is desirable. CCD detectors are commercially available from, e.g., Princeton Instruments, which can meet either of these requirements.

The detection device also can include a line scanner, as described in U.S. patent application Ser. No. 08/301,051, filed Sep. 2, 1994. Excitation optics focuses excitation light to a line at a sample, simultaneously scanning or imaging a strip of the sample. Surface-bound fluorescent labels from the array fluoresce in response to the light. Collection optics image the emission onto a linear array of light detectors. By employing confocal techniques, substantially only emission from the light's focal plane is imaged. Once a strip has been scanned, the data representing the 1-dimensional image are stored in the memory of a computer. According to one embodiment, a multi-axis translation stage moves the device at a constant velocity to continuously integrate and process data. Alternatively, galvometric scanners or rotating polyhedral mirrors may be employed to scan the excitation light across the sample. As a result, a 2-dimensional image of the sample is obtained.

In another embodiment, collection optics direct the emission to a spectrograph which images an emission spectrum onto a 2-dimensional array of light detectors. By using a spectrograph, a full spectrally resolved image of the array is obtained.

The read time for a polynucleotide array will depend on the photophysics of the fluorophore (i.e., fluorescence quantum yield and photodestruction yield) as well as the sensitivity of the detector. For fluorescein, sufficient signal-to-noise to read a chip image with a CCD detector can be obtained in about 30 seconds using 3 mW/cm$^2$ and 488 nm excitation from an Ar ion laser or lamp. By increasing the laser power, and switching to dyes such as CY3 or CY5 which have lower photodestruction yields and whose emission more closely matches the sensitivity maximum of the CCD detector, one easily is able to read each array in less than 5 seconds.

F. Data Analysis

Data generated in hybridization assays is most easily analyzed with the use of a programmable digital computer. The computer program generally contains a readable medium that stores the codes. Certain files are devoted to memory that includes the location of each feature and the sequence of the polynucleotide probe at that feature. Because analysis often involves comparing the sequence of a target to a reference sequence, the program also can include in its memory the reference sequence. Using this information, the program can then identify the set of features on the array whose probes define the reference sequence in the selected tiling strategy. The computer also contains code that receives as input hybridization data from a hybridization reaction between a target nucleic acid molecule and polynucleotide probes in the polynucleotide array. The computer also contains code that processes the hybridization data. The computer program also can include code that receives instructions from a programmer as input.

The computer can transform the data into another format for presentation. Data analysis can include the steps of determining, e.g., fluorescent intensity as a function of substrate position from the data collected, removing "outliers" (data deviating from a predetermined statistical distribution), and calculating the relative extent of binding of the targets from the remaining data. The resulting data can be displayed as an image with color in each region varying according to the light emission or extent of binding between targets and probes therein.

One application of this system when coupled with the CCD imaging system that speeds performance when the detection step involves hybridization of a labeled target polynucleotide with a polynucleotide in the array is to obtain results of the assay by examining the on- or off-rates of the hybridization. In one version of this method, the amount of binding at each address is determined at several time points after the targets are contacted with the array. The amount of total hybridization can be determined as a function of the kinetics of binding based on the amount of binding at each time point. Thus, it is not necessary to wait for equilibrium to be reached. The dependence of the hybridization rate for different polynucleotides on temperature, sample agitation, washing conditions (e.g., pH, solvent characteristics, temperature) can easily be determined in order to maximize the conditions for rate and signal-to-noise. Alternative methods are described in Fodor et al., U.S. Pat. No. 5,324,633, incorporated herein by reference.

The dependence of the hybridization rate for different polynucleotides on temperature, sample agitation, washing easily be determined in order to maximize the conditions for rate and signal-to-noise.

G. Mechanics of Assays

Assays on polynucleotide arrays generally include contacting a polynucleotide array with a labeled sample under the selected reaction conditions, optionally washing the array to remove unreacted molecules, and analyzing the biological array for evidence of reaction between target molecules the probes. These steps involve handling fluids. These steps can be automated using automated fluid handling systems for concurrently performing the detection steps on the array. Fluid handling allows uniform treatment of samples in the wells. Microtiter robotic and fluid-handling devices are available commercially, for example, from Tecan AG.

The chip can be manipulated by a fluid-handling device. This robotic device can be programmed to set appropriate reaction conditions, such as temperature, add reagents to the chip, incubate the chip for an appropriate time, remove unreacted material, wash the chip substrate, add reaction substrates as appropriate and perform detection assays. The particulars of the reaction conditions are chosen depends upon the purpose of the assay, for example hybridization of a probe or attachment of a label to polynucleotides.

If desired, the chip can be appropriately packaged for use in chip reader. One such apparatus is disclosed in U.S. patent application Ser. No. 08/255,682, filed Jun. 8, 1994.

H. Substrate-Associated Polynucleotide Array Manufacture

In making a chip, the substrate and its surface preferably form a rigid support on which the sample can be formed. The substrate and its surface are also chosen to provide appropriate light-absorbing characteristics. For instance, the substrate may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those skilled in the art upon review of this disclosure. In a preferred embodiment the substrate is flat glass or silica.

Surfaces on the solid substrate usually, though not always, are composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

Preferably, polynucleotides are arrayed on a chip in addressable rows and columns. Technologies already have been developed to read information from such arrays. The amount of information that can be stored on each chip depends on the lithographic density which is used to synthesize the wafer. For example, if each feature size is about 100 microns on a side, each chip can have about 10,000 probe addresses (features) in a 1 $cm^2$ area.

The following examples are offered by way of illustration, not by way of limitation.

EXAMPLE

The method of the invention was used to screen for new members of the TGF-β superfamily of proteins. There are currently 32 known members of this family. Clone libraries were created from genomic material based on hybridization to: nucleic acid probes in solution that contain sequences complementary to sequence motifs that are indicative of members of this gene family. The genomic inserts were approximately 15 kb in size. Most of the inserts contain sequences from previously known members of the family.

Conventional approaches involve sequencing these 15 kb inserts over and over, most of the time only to find that the insert contains a family member that has already been identified. The method of this invention replaced those laborious and time consuming steps with a faster, easier screening method that can identify which clones contain known members of the family, and which few clones out of the large library are worth investigating in greater detail.

TGF-β Clone Screening Polynucleotide Array:

The array contained over 12,000 features with different probes with single-increment, 4-base trellis tilings for 99 bases for each of the 32 known members of the TGF-β family (see FIG. 5) The 99 bases were from 4 different regions of the genes and the contiguous regions range in size from 18 to 30 bases. The interrogated regions were chosen based on a few criteria: they include regions that are (a) reasonably well conserved (highly conserved at the amino acid level, but less so at the DNA level) and that serve as identifiers of the protein family, (b) highly variable and serve as unique identifiers of individual members of the family, and (c) not near expected intron/exon boundaries.

TGF-β Clone Samples for Hybridization:

Either DNA or RNA can be produced from a clone using standard methods, e.g., nucleic acid extractions followed by PCR or in vitro transcription, with labeled bases incorporated during the polymerization step. Fragmented single-stranded DNA or RNA can be-used in the hybridization as well as fragmented double stranded DNA. The hybridizations are done in either 6×SSPE-T or 3M TMACl-T (buffered with Tris to avoid having any Na ions in the hybridization solution), and generally at temperatures above 30° C. to improve discrimination and to reduce cross-hybridization (this is more important in this application than for some re-sequencing applications because the samples include ~15,000 bases). If labeled RNA is used, samples are fragmented with heat in the presence of $Mg^{2+}$. If DNA is used, samples are fragmented by treatment with DNAse I prior to hybridization. This works with both double stranded DNA or with DNA that is made single-stranded following PCR by degradation of one of the strands using lambda exonuclease.

Examples and Data Analysis:

Following hybridization and reading of the arrays, the images were analyzed using the TGF report GeneChip software (Affymetrix, Inc., Santa Clara, Calif., USA). Base calls were made over all 99 bases for each of the 32 different regions. The calls were compared with the sequences expected for each of the 32 known wild type sequences (see FIGS. 5 and 6). For each, the results of the base calling were listed, and the output was sorted based on the number of calls (# correct) that match the expected sequence in that region. In all the cases to date, when known sequences have been hybridized, the correct sequence was at the top of the list. Additionally, the software gives a detailed assessment of the base calls in each of the four different regions for the top five sequences in the list, giving a clearer picture of where the similarities and differences occur. Result of hybridization between the array and DNA from hBMP-7 and hBMP-5 is shown in FIG. 6.

Diagnosis of a disease is made by obtaining a sample of bodily fluids, tissue, or other nucleic-acid containing material and determines whether a sequence signature present in a possible pathogen or set of pathogens is present. For example, one determining whether a sequence signature of a mycobacterium is present using the methods taught on PCT publication No. WO97/29212. If no mycobacterium is present, the presence of another suspected pathogen is explored.

The present invention provides a novel method for performing assays on polynucleotide arrays. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for analyzing a mRNA, said mRNA comprising one or more exons having an order, said order defined by one or more sequence signatures, each said one or more sequence signatures comprising a sequence spanning two exons, said method comprising;

providing said mRNA;

processing said mRNA to provide labeled nucleic acid fragments corresponding to said exons and said sequence signatures;

hybridizing said labeled fragments to a nucleic acid array, wherein said nucleic acid array comprises probes corresponding to said one or more exons and to said one or more sequence signatures; and determining the identity of said sequence signatures and order of each said one or more exons to analyze the mRNA.

2. A method according to claim 1 further comprising generating data concerning which probes have bound to which labeled fragments and using computer programs to process said data to determine the identity and order of each said one or more exons.

3. A method according to claim 1 wherein said nucleic acid array is a high density polynucleotide array.

4. A method according to claim 1, wherein said step of processing is accomplished by in vitro transcription of a reverse transcribed double stranded DNA having a promoter with labeled bases incorporated during the incorporation step.

5. A method according to claim 4, wherein following said in vitro transcription the labeled RNA is fragmented.

6. A method according to claim 3 wherein said high density oligonucleotide array has a density selected from the group of 625, 1000, 10,000, 1,000,000 and 10,000,000 features per square cm.

7. A method according to claim 1 wherein said sequence signature includes sequences at most 300, 250, 200, 150, 100, 75, 50, 30, 25 or at most 15 nucleotides.

8. A method according to claim 1 wherein said sequence signatures include sequences less than 10, 15, 25, 30, 35, 45, 50, 60, 70, 80, 90, 100, 120, 135, 150, 175, 200, 250 and 300 nucleotides long.

9. A method according to claim 1 wherein said sequence signature includes the Hogness box, the TATA box, a homeobox, the CAAT box and ALU repeat sequences.

* * * * *